(12) United States Patent
Madabhushi et al.

(10) Patent No.: US 11,576,640 B2
(45) Date of Patent: Feb. 14, 2023

(54) FRACTAL ANALYSIS OF LEFT ATRIUM TO PREDICT ATRIAL FIBRILLATION RECURRENCE

(71) Applicants: Case Western Reserve University, Cleveland, OH (US); The Cleveland Clinic Foundation, Cleveland, OH (US)

(72) Inventors: Anant Madabhushi, Shaker Heighls, OH (US); Marjan Firouznia, Cleveland Heights, OH (US); Mina K. Chung, Shaker Heights, OH (US); Albert Feeny, Cleveland Heights, OH (US)

(73) Assignees: Case Western Reserve University, Cleveland, OH (US); The Cleveland Clinic Foundation, Cleveland, OH (US)

( * ) Notice: Subject to any disclaimer, the term of this patent is extended or adjusted under 35 U.S.C. 154(b) by 319 days.

(21) Appl. No.: 17/034,673

(22) Filed: Sep. 28, 2020

(65) Prior Publication Data
US 2021/0093281 A1 Apr. 1, 2021

Related U.S. Application Data
(60) Provisional application No. 62/906,181, filed on Sep. 26, 2019.

(51) Int. Cl.
*A61B 6/00* (2006.01)
*G06T 7/00* (2017.01)
(Continued)

(52) U.S. Cl.
CPC ............ *A61B 6/5217* (2013.01); *A61B 6/032* (2013.01); *A61B 6/503* (2013.01); *G06T 7/0012* (2013.01);
(Continued)

(58) Field of Classification Search
CPC ....... A61B 6/5217; A61B 6/52; A61B 6/5211; A61B 6/5205; A61B 6/503; A61B 6/504; A61B 6/50; A61B 6/032; G06T 7/0012; G06T 7/48; G06T 7/41; G06T 2207/10081; G06T 2207/20081; G06T 2207/20084; G06T 2207/30048; G06T 2207/30101
See application file for complete search history.

(56) References Cited

U.S. PATENT DOCUMENTS

2017/0319278 A1* 11/2017 Trayanova ............. A61B 6/032
2018/0075600 A1*  3/2018 Cales ........................ G06T 7/90
2022/0101530 A1*  3/2022 Trayanova ............. G16H 30/40

* cited by examiner

*Primary Examiner* — Carolyn A Pehlke
(74) *Attorney, Agent, or Firm* — Eschweiler & Potashnik, LLC

(57) ABSTRACT

Embodiments discussed herein facilitate determination of risk of recurrence of atrial fibrillation (AF) after ablation based on fractal features. One example embodiment is configured to generate a binary mask of at least a portion of a CT scan of a heart of a patient with AF; compute one or more radiomic fractal-based features from at least one of the binary mask or the portion of the CT scan; provide the one or more radiomic fractal-based features to a trained machine learning (ML) classifier; and receive a prediction from the trained ML classifier of whether or not the AF will recur after AF ablation, wherein the prediction is based at least in part on the one or more radiomic fractal-based features.

20 Claims, 21 Drawing Sheets

(51) Int. Cl.
*A61B 6/03* (2006.01)
*G16H 30/20* (2018.01)

(52) U.S. Cl.
CPC ... *G16H 30/20* (2018.01); *G06T 2207/10081* (2013.01); *G06T 2207/20081* (2013.01); *G06T 2207/30048* (2013.01); *G06T 2207/30101* (2013.01)

F8:3D_shape_median (F<sub>LA</sub>), F21:3D_shape_median (F<sub>PV</sub>),
F14:Mean_FD2_shape (F<sub>PV</sub>), F28:3D_texture_skewness (F<sub>LAM</sub>),
F10: Entropy shape (F<sub>LA</sub>).

FRACTAL ANALYSIS OF LEFT ATRIUM TO PREDICT ATRIAL FIBRILLATION RECURRENCE

CROSS REFERENCE TO RELATED APPLICATIONS

This application claims the benefit of U.S. Provisional Patent Application No. 62/906,181 filed Sep. 26, 2019, entitled "FRACTAL ANALYSIS OF LEFT ATRIUM TO PREDICT ATRIAL FIBRILLATION RECURRENCE", the contents of which are herein incorporated by reference in their entirety.

BACKGROUND

Atrial Fibrillation (AF) is a common cardiac arrhythmia that affects 1-2% of the population in which rapid and irregular electrical atrial activation causes loss of synchronized contractions of the atria. AF is predicted to affect 6-12 million people in the USA by 2050 and 17.9 million in Europe by 2060. AF is associated with significant morbidity, including increased risk of stroke, heart failure and death. AF consumes significant health resources and is associated with a fourfold to fivefold increased risk of thromboembolic events. Among patients who experience strokes, AF is associated with 1.5% of strokes at 50 years of age and 23.5% at 80 years. Although catheter ablation is an invasive technique to treat AF with pulmonary vein (PV) isolation, AF recurrence rates after ablation are high, indicating a need for improved prediction of AF recurrence and ablation targets.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Various embodiments discussed herein can train and/or employ a machine learning classifier to predict recurrence or non-recurrence of atrial fibrillation after ablation. Various embodiments can predict and/or be trained to predict based at least in part on one or more radiomic fractal-based features discussed herein, and optionally based at least in part on one or more clinical features.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
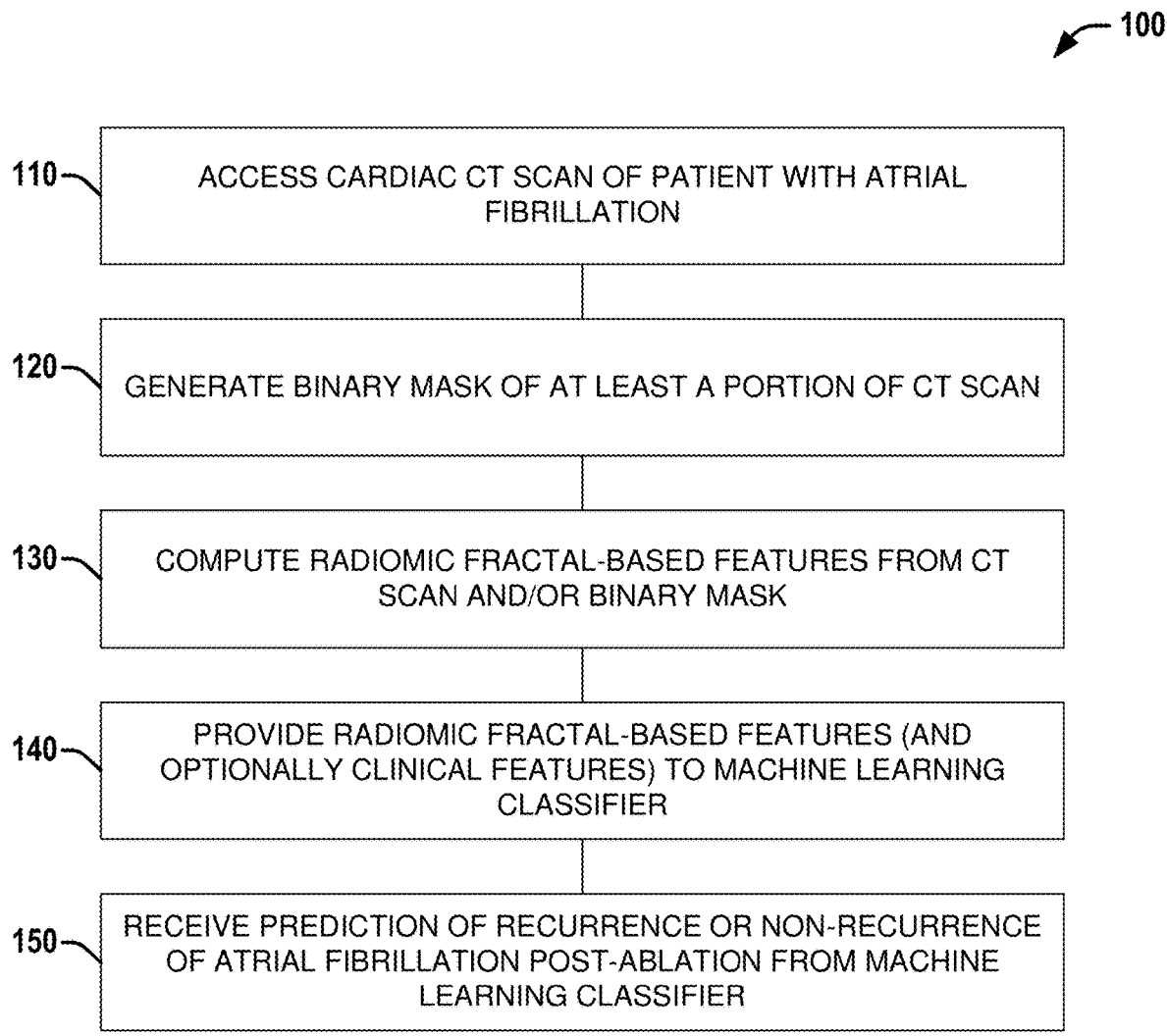
FIG. 1 illustrates a flow diagram of an example method/set of operations that can be performed by one or more processors to predict whether or not atrial fibrillation (AF) will recur post-ablation based at least in part on one or more radiomic fractal-based features, according to various embodiments discussed herein.

Referring to FIG. 1, illustrated is a flow diagram of an example method/set of operations 100 that can be performed by one or more processors to predict whether or not atrial fibrillation (AF) will recur post-ablation based at least in part on one or more radiomic fractal-based features, according to various embodiments discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing a cardiac CT scan of a patient with AF. In various embodiments and in the example use case discussed below, the CT scan can be obtained via a system and/or apparatus implementing the set of operations 100, or can be obtained from a separate medical imaging system (e.g., a CT system/apparatus). Additionally, the CT scan can be accessed contemporaneously with or at any point prior to performing the set of operations 100.

The set of operations 100 can further comprise, at 120, generating a binary mask of at least a portion of the cardiac CT scan. In various embodiments, the portion of the cardiac CT scan can be based on one or more of the models discussed herein (e.g., left atrium wall, left atrium body and ostia of pulmonary veins, left atrium lumen and full structure of pulmonary veins, etc.).

The set of operations 100 can further comprise, at 130, computing one or more radiomic fractal-based features from at least one of the binary mask or the portion of the CT scan.

The set of operations 100 can further comprise, at 140, providing the computed radiomic fractal-based features (and optionally one or more clinical features) to a machine learning classifier constructed to predict AF recurrence or non-recurrence based on the provided features.

The set of operations 100 can further comprise, at 150, receiving a prediction of recurrence or non-recurrence of AF post-ablation from the machine learning classifier.

Figure 2:
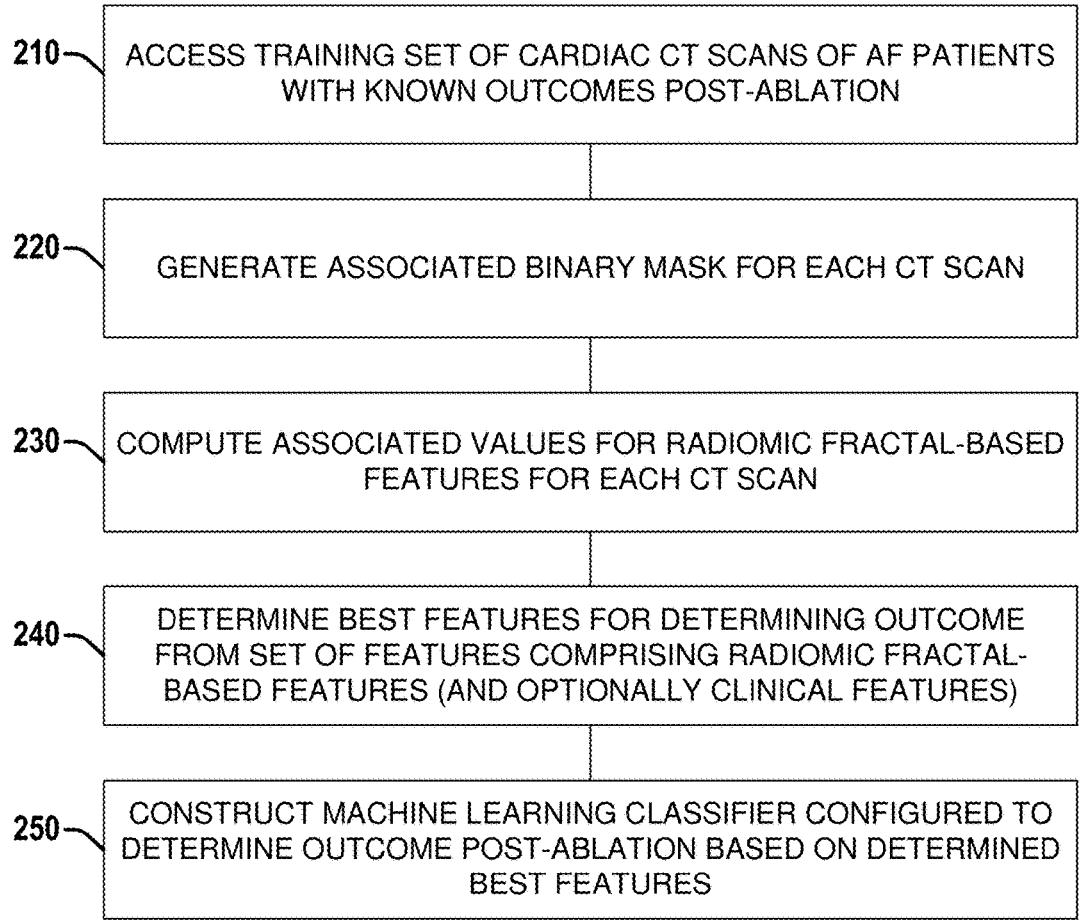
FIG. 2 illustrates a flow diagram of an example method/set of operations that can be performed by one or more processors to construct a machine learning classifier to generate a prediction of recurrence or non-recurrence of atrial fibrillation post-ablation based at least in part on one or more radiomic fractal-based features, according to various aspects discussed herein.

Referring to FIG. 2, illustrated is a flow diagram of an example method/set of operations 200 that can be performed by one or more processors to construct a machine learning classifier to generate a prediction of recurrence or non-recurrence of atrial fibrillation post-ablation based at least in part on one or more radiomic fractal-based features, according to various aspects discussed herein.

The set of operations 200 can comprise, at 210, accessing a training set of cardiac CT scans of patients with AF and known post-ablation outcomes of recurrence or non-recurrence of AF. In various embodiments and in the example use case discussed below, the training set of CT scans can be obtained via a system and/or apparatus implementing the set of operations 200, or can be obtained from a separate medical imaging system. Additionally, the training set can be accessed contemporaneously with or at any point prior to performing the set of operations 200.

The set of operations 200 can further comprise, at 220, generating an associated binary mask of at least a portion of each CT scan of the training set.

The set of operations 200 can further comprise, at 230, computing associated values for each of a plurality of radiomic fractal-based features for each CT scan based on the associated binary mask and/or the portion of the CT scan.

The set of operations 200 can further comprise, at 240, determining a plurality of best features for determining recurrence or non-recurrence of AF post-ablation from among a set of features comprising the radiomic fractal-based features (and optionally one or more clinical features).

The set of operations 200 can further comprise, at 250, constructing a machine learning classifier configured to predict a post-ablation outcome for AF based on the determined best features.

Additional aspects and embodiments are discussed below in connection with the following example use cases.

Example Use Case 1: Machine Learning Derived Fractal Features of Shape and Texture of the Left Atrium and Pulmonary Veins from Cardiac CT Scans are Associated with Risk of Recurrence of Atrial Fibrillation Post-Ablation The following discussion provides example embodiments in connection with a first example use case involving training, validation, and testing of machine learning models to predict recurrence of atrial fibrillation based at least in part on fractal features.

Background: Left atrium (LA) remodeling may increase likelihood of recurrent atrial fibrillation (AF) after catheter ablation. The first example use case hypothesized that computerized morphologic analysis of the LA and pulmonary veins (PVs) via fractal measurements of shape and texture features of the LA myocardial wall could predict AF recurrence after ablation.

Methods: Pre-ablation contrast CT scans were collected for 203 patients who underwent AF ablation. The LA body, PVs, and LA myocardial tissue were segmented using a semi-automated region growing method. 28 fractal-based shape and texture-based features were extracted from resulting segments. The top 5 features most associated with post-ablation recurrence were identified using feature selection and subsequently evaluated with a Random Forest classifier. Feature selection and classifier construction were performed on a discovery cohort ($D_1$) of 137 patients; classifiers were subsequently validated on an independent set ($D_2$) of 66 patients. Dedicated classifiers to capture the fractal and morphologic properties of LA body ($C_{LA}$), PVs ($C_{PV}$), and LA myocardial ($C_{LAM}$) tissue were constructed, as well as a model ($C_{AII}$) capturing properties of all segmented compartments. Fractal-based models were also compared against a model employing machine estimation of LA volume. To assess the effect of clinical parameters, such as AF type and catheter technique, a clinical model ($C_{clin}$) was also compared against $C_{AII}$.

Results: Statistically significant differences were observed for fractal features of $C_{LA}$, $C_{LAM}$ and $C_{AII}$ in distinguishing AF recurrence (p<0.001) on $D_1$. Using the 5 top features, $C_{AII}$ had the best prediction performance (AUC=0.81), followed by $C_{PV}$ (AUC=0.78) and $C_{LA}$ (AUC=0.70) on $D_2$. The clinical parameter model $C_{clin}$ yielded an AUC=0.70, while the atrial volume model yielded an AUC=0.59. Combining $C_{AII}$ and $C_{clin}$ on $D_2$ improved the AUC to 0.87.

Conclusion: Fractal measurements of the LA, PVs, and atrial myocardium on CT scans were associated with likelihood of post-ablation AF recurrence.

Introduction

Atrial fibrillation (AF) is a common cardiac arrhythmia that affects 1-2% of the population. During AF, rapid and irregular electrical atrial activation causes loss of synchronized atrial contractility. AF is associated with significant morbidity, including increased risk of stroke, heart failure and death. Catheter ablation is an invasive technique to treat medically-refractory or symptomatic AF through pulmonary vein (PV) isolation and/or substrate ablation, though recurrence rates are high, indicating a need for improved prediction of AF recurrence and ablation targets.

AF induces morphological changes of the left atrium (LA), which can manifest as changes in atrial volume, shape, the atrial wall, and PVs. Remodeling of these structural changes after AF ablation has been detected using computed tomography (CT). Several models have been proposed to predict AF recurrence after ablation using clinical features, such as age, hypertension, and persistence of AF and LA scarring. Further investigation into the different LA morphologies associated with AF recurrence support the use of imaging in identifying patients for ablation. Several investigators have reported that LA geometry has an important role in assessing AF incidence and recurrence using various cardiac imaging modalities. Cardiac CT can assess atrial wall thickness and PV and LA anatomy before catheter ablation procedures for AF. One group demonstrated that shape features of LA can be useful for predicting AF recurrence from screening CT scans, and a second group reported that enlarged PVs by magnetic resonance imaging (MRI) predicted AF recurrence after ablation. A third group demonstrated that changes in myocardial structure in the LA are an important part of this pathological remodeling process.

Although Euclidean geometry is useful for describing smooth and regular shapes, fractal dimension provides a novel approach to quantitatively characterize irregularity or roughness in shape and texture. Complex biologic structures have self-similar properties that enable them to be quantified by their fractal dimension (FD). FD measurements have been previously employed for teasing out subtle morphometric differences between normal and pathologically compromised anatomical structures on medical imaging scans.

The objective of the first example use case was to evaluate the role of fractal related features pertaining to shape and textural differences of the LA and PVs on pre-treatment CT scans between AF patients with or without recurrent AF following ablation.

Methods

The first example use case first extracted fractal features to characterize morphological and texture variation of the LA and PVs. Fractal based classification models were constructed individually for the LA and PV models. A combined model involving features from both LA and PVs was also constructed. Fractal features were then used to develop a random forest machine classifier to predict the likelihood of AF recurrence from CT scans. The first example use case evaluated whether fractal features provided additional predictive value beyond clinical variables, including age, sex, LA volume, left ventricular ejection fraction (LVEF), body mass index (BMI), hypertension, sinus rhythm at time of ablation, AF type (paroxysmal, persistent), and ablation type (irrigated radiofrequency, cryoballoon ablation). Models were tested on an independent set.

Figure 3:
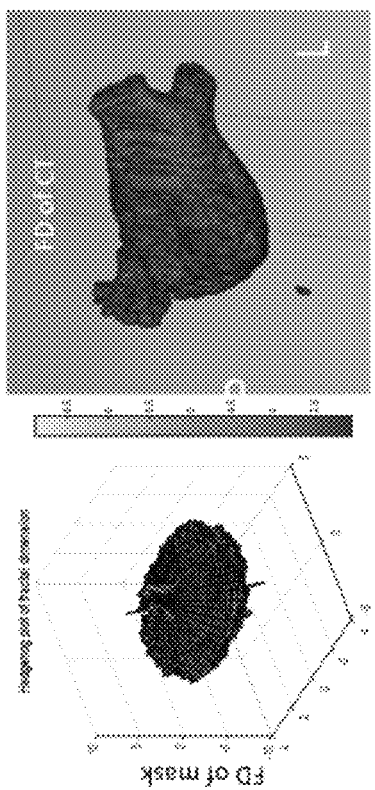
FIG. 3 illustrates ample images and charts showing an overview of the methodology of the first example use case, in connection with various aspects discussed herein.
Figure 3:
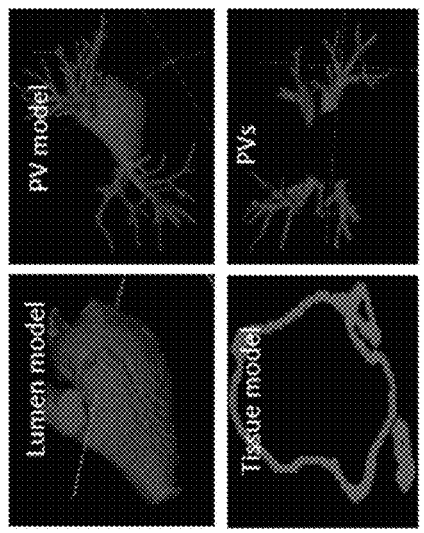
Figure 3:
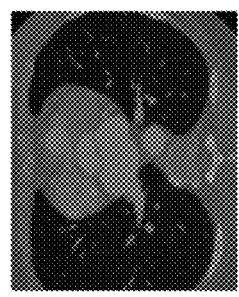
Figure 3:
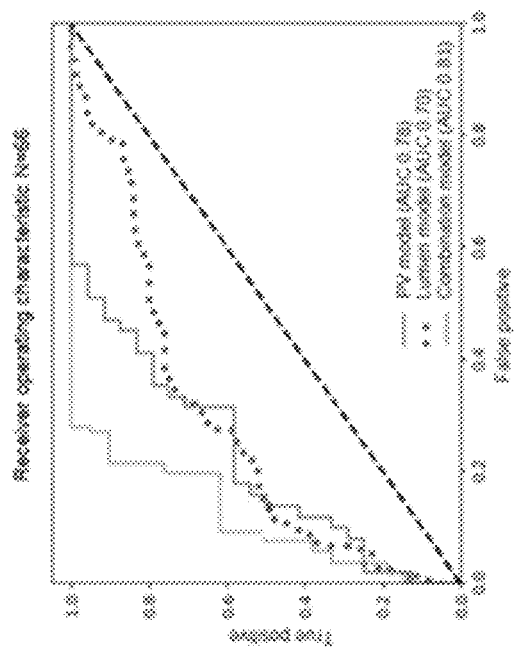
Figure 3:
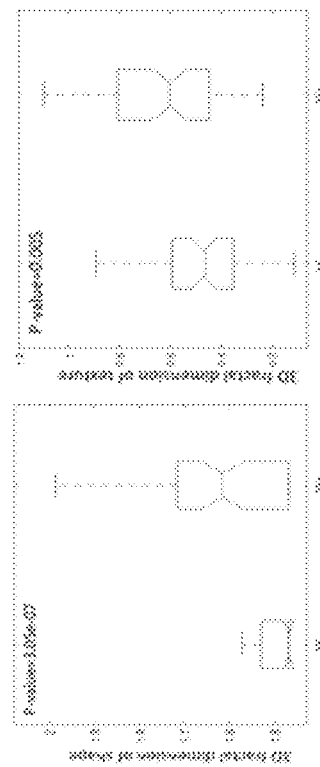

Referring to FIG. 3, illustrated are example images and charts showing an overview of the methodology of the first example use case, in connection with various aspects discussed herein. CT images were retrospectively collected (310). Regions of interest were segmented using clinical software (Syngo.Via) to obtain segmented masks for all models (320). Three-dimensional (3D) fractal features were extracted from the LA and PV segmentations (330). Next, Wilcoxon rank-sum tests were used to select the top features (340) to train a random forest classifier and validate it (350) on an independent dataset (n=66). Receiver operating characteristic (ROC) curves of the fractal-based radiomic classifier were trained on 203 patients with 137 patients for training ($D_1$) and 66 patients for testing ($D_2$). The different classifier models including those for the LA body, PV, and the combined model $C_{AII}$ were evaluated on $D_2$ using ROC curve analysis. The details of LA body, PV, and tissue model are shown in table 1, below.

TABLE 1

| Segmentation models | |
|---|---|
| Models | Properties |
| Lumen model | The left atrium body and the ostia of the PVs. |
| PV model | Left atrial lumen and branching structures of PVs. |

TABLE 1-continued

Segmentation models

| Models | Properties |
|---|---|
| Tissue model | The LA myocardial tissue model comprises the LA wall. |

Patient Population

Figure 4:
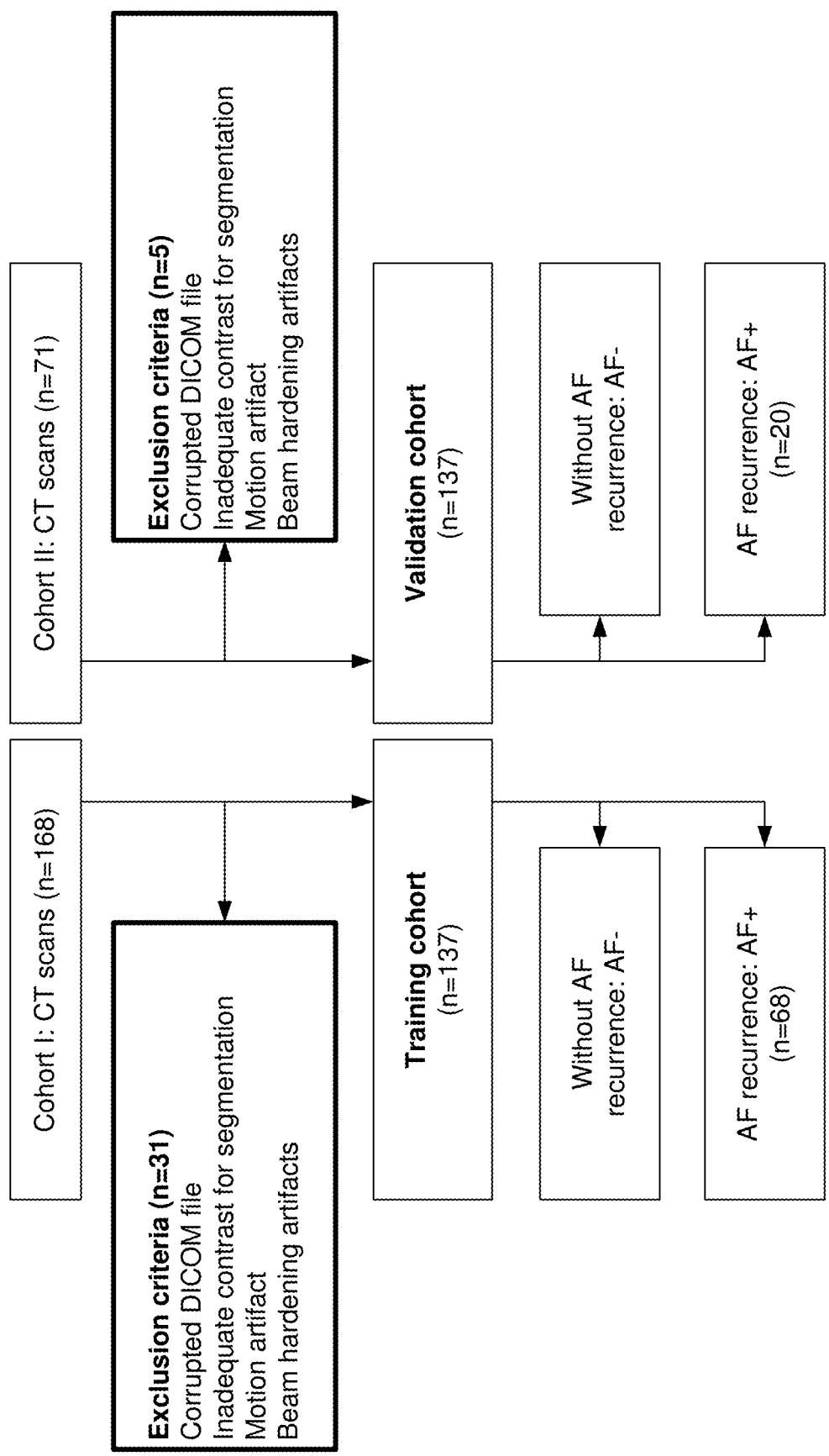
FIG. 4 illustrates a flowchart showing inclusion and exclusion criteria for the first example use case, in connection with various aspects discussed herein.

The first example use case a retrospective study involving two cohorts of patients with AF who underwent catheter ablation, each with routine pulmonary vein CT scans prior to ablation. Referring to FIG. 4, illustrated is a flowchart showing inclusion and exclusion criteria for the first example use case, in connection with various aspects discussed herein. The first cohort comprised all eligible patients who underwent ablation between 2013-2016. The second cohort comprised patients in a registry to study lone AF who underwent ablation between 2003-2009. Patients with prior ablation, congenital heart disease, and valvular disease were excluded because these conditions are significant confounders, independent of LA/PV morphology, for ablation success rate. Patients with CT scans with excessive artifacts or poor contrast (see FIG. 4) that hindered the ability to accurately segment the different tissue compartments were also excluded. In all from a total of 239 patients, 36 patients were excluded, as shown in the flowchart for inclusion and exclusion criteria in FIG. 4. A discovery cohort ($D_1$) of 137 patients was identified from the ablation cohort from 2013-2016, and the independent validation set ($D_2$) of 66 patients was constructed from the lone atrial fibrillation cohort from 2003-2009. Table 2, below, shows the patient characteristics of the two cohorts.

TABLE 2

Patient Characteristics of $D_1$ and $D_2$ for $C_{clin}$

| Characteristics | | $D_1$ | $D_2$ |
|---|---|---|---|
| Age | | 64 | 56 |
| Sex (male) | | 103 | 53 |
| Height | | 176.4671 | 179.9242 |
| Weight | | 94.9145 | 97.1818 |
| CAD | | 28 | — |
| Hypertension | | 80 | — |
| Diabetes | | 28 | — |
| Left Ventricular Ejection Fraction | | 55.9 | 55.1515 |
| AFib Type (Paroxysmal) | | 84 | 40 |
| Ablation Energy Type | Cryo Ablation | 41 | 0 |
| | Radiofrequency | 100 | 66 |

LA Segmentation and Feature Extraction

Binary segmentation models were created in Syngo.Via (Siemens, Munich, Germany) imaging software using a semi-automated 3D region growing algorithm. The user selects a seed point within the lumen of the LA to initiate region growing. This constructs a local segmentation by aggregating neighboring regions of similar CT intensities. Iteratively selecting new seed points, several local segmentations are created which are then ensembled to create a unified segmentation of the LA body, LA appendage, and full branching structure of the PVs. Areas of erroneous segmentation were manually edited by the user. The branching structures of the PVs were trimmed down to the PV ostia, and the remaining segmentation was saved as the LA body model. The LA body model was uniformly expanded to include the myocardial wall just outside of the contrast-filled lumen. The original LA body model was then subtracted from the expanded LA body model to leave only the LA wall. The segmentation models are depicted in FIG. 3 at 320. The binary segmentation models corresponding to the PV and LA were subsequently exported to MATLAB 2018b (Mathworks, Natick, Mass.) for additional feature analysis.

Fractal Analysis

Shape-Based Features of LA and PVs

1 D, 2D, and 3D fractal dimensions were extracted to assess shape related features of the LA. Fractal dimension (FD) is defined as the negative gradient of an ordinary least-squares fit line to the logarithm of box size and box count. Higher values of FDs are reflective of greater levels of anatomic complexity and surface variation. The 1D fractal feature was extracted as a time series measurement from each individual slice from within the 3D volume, which can be generated using the distance between boundary and central pixels. The 1D fractal dimension describes the edge information of the volume. 2D fractal dimension features of the segmented LA body were calculated by using a standard fully automated box-counting method, in which the mask is overlaid on a grid of known box size, and the number of boxes containing nonzero image pixels is recorded (the box count). This process was repeated with box sizes between two pixels and 50% of the image size. The LA borders were detected using the Canny edge detector. 2D fractal dimensions were derived from borders of each slice by using the box-counting method. 3D fractal dimension as a shape-based feature describes the degree and direction of anisotropy. For 3D fractal analysis of segmentation mask, spectral density (SD) analysis was applied using MATLAB code developed for a previous study. A more detailed description of 1 D, 2D and 3D features is provided in Table 3. A total of 26 shape-based features that were extracted from the PV and LA body models.

TABLE 3

The details of 1D, 2D, and 3D fractal dimensions

| Main features | | Method | Extracted from | Characteristics |
|---|---|---|---|---|
| MF1 | 1D fractal dimension | Converting the image to time series and calculating FD. | mask | Shape |
| MF2 | 2D fractal dimension | Box-counting of each slice of CT scans | mask | Shape |
| MF3 | 3D fractal dimension of segmentation mask (shape-based feature) | Spectral density (SD) analysis was performed using MATLAB code | mask | Shape |
| MF4 | 3D fractal dimension of CT scans (texture-based feature) | employing the 3D fast Fourier transform (FFT) | CT scans | Texture |

Texture features of Tissue model: Two fractal features related to texture variations of CT intensities in the LA wall were also extracted. This was done by employing the 3D fast Fourier transform (FFT) of fractal dimension. The CT scans were transformed to FD images using the differential box-counting (DBC) algorithm. The fractal dimension image was generated by considering each pixel in the original CT image as a single fractal dimension estimated from its 7×7 neighbors.

Statistical Analysis

A total of 28 features (26 shape features, 2 texture features) were extracted, detailed in Table 4, below.

TABLE 4

28 Fractal Features

| Model | Features | Explanation | p-values |
|---|---|---|---|
| Left atrium | F1: Mean_FD2_shape | Mean of MF2 | 0.0007 |
| | F2: Median_FD2_shape | Median of MF2 | 0.06 |
| | F3: Skewness_FD2_shape | Skewness of MF2 | 0.3 |
| | F4: Maximum_FD2_shape | Maximum of MF2 | 0.05 |
| | F5: 3D_shape_aveg | Average of MF3 | 0.8 |
| | F6: 3D shape_std | Standard derivation of MF3 | 0.007 |
| | F7: 3D_shape_skewness | Skewness of MF3 | 0.003 |
| | F8: 3D_shape_median | Median of MF3 | 0.000003 |
| | F9: Entropy_boundary | Entropy of LA using time series | 0.0004 |
| | F10: Entropy_shape | Entropy of LA | 0.09 |
| | F11: GMM_C1 | First component of Gaussian mixture model | 0.6 |
| | F12: GMM_C2 | Second component of Gaussian mixture model | 0.01 |
| | F13: GMM_C3 | Third component of Gaussian mixture model | 0.0009 |
| PV | F14: Mean_FD2_shape | Mean of MF2 | 0.0001 |
| | F15: Median_FD2_shape | Median of MF2 | 0.07 |
| | F16: Skewness_FD2_shape | Skewness of MF2 | 0.03 |
| | F17: Maximum_FD2_shape | Maximum of MF2 | 0.07 |
| | F18: 3D_shape_aveg | Average of MF3 | 0.004 |
| | F19: 3D shape_std | Standard derivation of MF3 | 0.04 |
| | F20: 3D_shape_skewness | Skewness of MF3 | 0.002 |
| | F21: 3D_shape median | Median of MF3 | 0.00002 |
| | F22: Entropy_boundary | Entropy of LA using time series | 0.0003 |
| | F23: Entropy_shape | Entropy of LA | 0.1 |
| | F24: GMM_C1 | First component of Gaussian mixture model | 0.08 |
| | F25: GMM_C2 | Second component of Gaussian mixture model | 0.02 |
| | F26: GMM_C3 | Third component of Gaussian mixture model | 0.0005 |
| LA wall | F27: 3D_texture_mean | Mean of MF4 | 0.02 |
| | F28: 3D_texture_skewness | Skewness of MF4 | 0.0005 |

Feature selection was implemented to avoid the curse of dimensionality and reduce the risk of model overfitting. The variable ranking feature selection was used to identify the top 5 most discriminating features with the lowest p-value (<0.001, using the Wilcoxon rank sum tests) for each of the individual models in $D_1$, followed by training a Random Forest (RF) classifier in conjunction with these top identified features. Dedicated random forest classifiers to capture the fractal and morphologic properties of LA body ($C_{LA}$), PVs ($C_{PV}$), and LA myocardial ($C_{LAM}$) tissue were constructed, as well as model ($C_{All}$) capturing the associated properties of all the segmented compartments. To evaluate the predictive contribution of the PV alone, an additional classifier model ($C_{PV-LA}$) was created by subtracting the PV segmentation from the segmentation of the left atrium, leaving only the branching structures of the pulmonary veins and the Left Atrial Appendage (see FIG. 3). A machine model ($C_{LAV}$) employing computer estimated left atrium volume from the individual segmentations of the LA was also constructed in order to compare a previous approach with $C_{All}$, $C_{PV}$, $C_{LA}$. The Statistical Parametric Mapping (SPM) toolbox was used to estimate the volume of LA from CT scans.

An integrated clinical and FD model ($C_{Clin+FD}$) was also created. For $C_{Clin+FD}$, the features used were the 5 top selected FD features including 2 shape-based features from the PV model, 2 shape-based features from the Lumen, one 3D texture feature, and 4 clinical parameters including Age, AF type, Hypertension, and catheter technique.

The different models were all validated on the independent test set D2 (n=66). The various models were compared in terms of area (AUC) under the receiver operating characteristic curve (ROC).

Results

Experiment 1: Evaluate the Role of Fractal Related Features of the Individual Chambers/Compartments of the Heart in their Association with Likelihood of Post-Ablation AF Recurrence To characterize morphological and texture variation of the LA in patients, 28 fractal features were extracted from the training set, including 13 fractal features from PV, 13 fractal features from LA, and 2 texture-based features from LA wall. P-values of the shape and texture-based features were evaluated to identify significant features using Wilcoxon rank sum test. To assess the role of the fractal features and main differences between patients with AF recurrence (AF+) and without AF recurrence (AF−), 3D fractal features were extracted.

Figure 5:
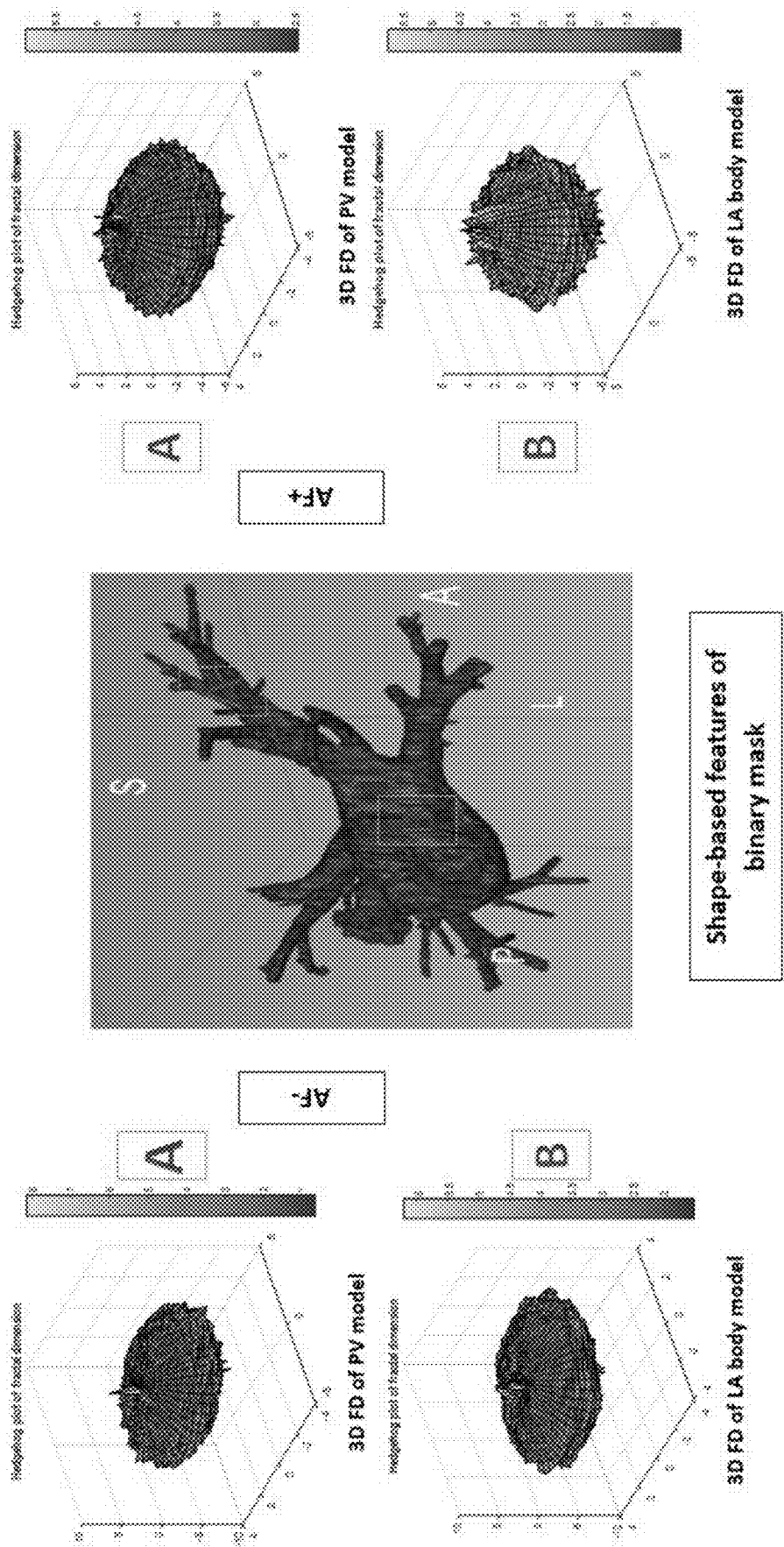
FIG. 5 illustrates an example image and charts showing 3D shape-based fractal features extracted from segmentation masks of LA and PVs, in connection with various aspects discussed herein.
Figure 6:
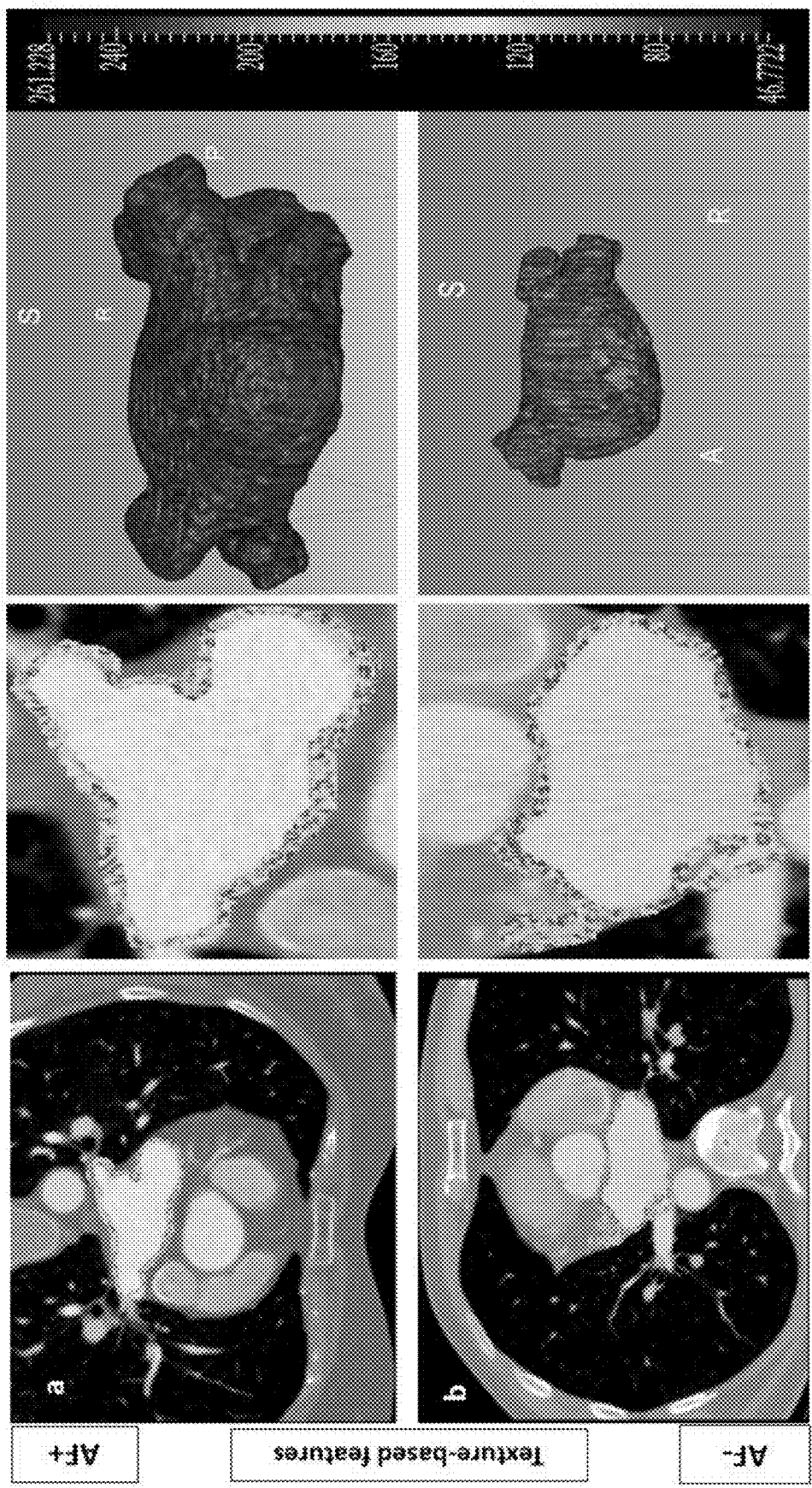
FIG. 6 illustrates example images showing 3D texture-based fractal features of the myocardial wall of LA extracted from CT scans, in connections with various aspects discussed herein.

Referring to FIG. 5, illustrated is an example image and charts showing 3D shape-based fractal features extracted from segmentation masks of LA and PVs, in connection with various aspects discussed herein. Images show feature extraction from masks using 3D fractal features to characterize shape of LA body and PV models. The top row of charts (labeled A) relate to the PV model of LA, comprising the LA body and PVs, and the bottom row of charts relate to the LA body model, comprising the LA body, appendage, and pulmonary vein ostia. Images show 3D fractal analysis of LA body and PV masks in patient with AF recurrence (AF+) and without AF recurrence (AF−). Referring to FIG. 6, illustrated are example images showing 3D texture-based fractal features of the myocardial wall of LA extracted from CT scans, in connections with various aspects discussed herein. The images of FIG. 6 show 3D fractal features of CT scans and 3D heatmaps of the features. 3D fractal dimension represents texture information of the myocardial tissue of LA. The top row of FIG. 6 shows a CT scan, FD features, and FD heat map of the patient with AF recurrence (AF+), and the bottom row shows a CT scan, FD features, and FD heat map of a patient without AF recurrence (AF−).

3D fractal based shape features from LA and PVs and 3D fractal based texture features from the LA wall were considered to discriminate between AF+ and AF− patients. 3D shape-based features from LA and PV were extracted as illustrated in FIG. 5. The 3D fractal shape analysis of PV and LA body models are illustrated in FIG. 6. The fractal texture features were found to be significantly different between AF+ and AF− patients (p-value<0.001). As illustrated in FIG. 6, patients with AF recurrence tended to have a higher expression of 3D fractal features (see Table 4).

As shown in FIG. 5, AF− patients tend to have a lower fractal dimension, whereas AF+ patients tend to have a higher fractal dimension, the higher FD values reflecting greater levels of anatomic complexity and surface variation. FIG. 6 shows 3D fractal analysis of myocardial wall to characterize texture variations. The heat maps in FIG. 6 show significant differences in 28 fractal features between AF+ and AF− patients, the feature expression being higher in AF+ compared to AF− patients.

Figure 7:
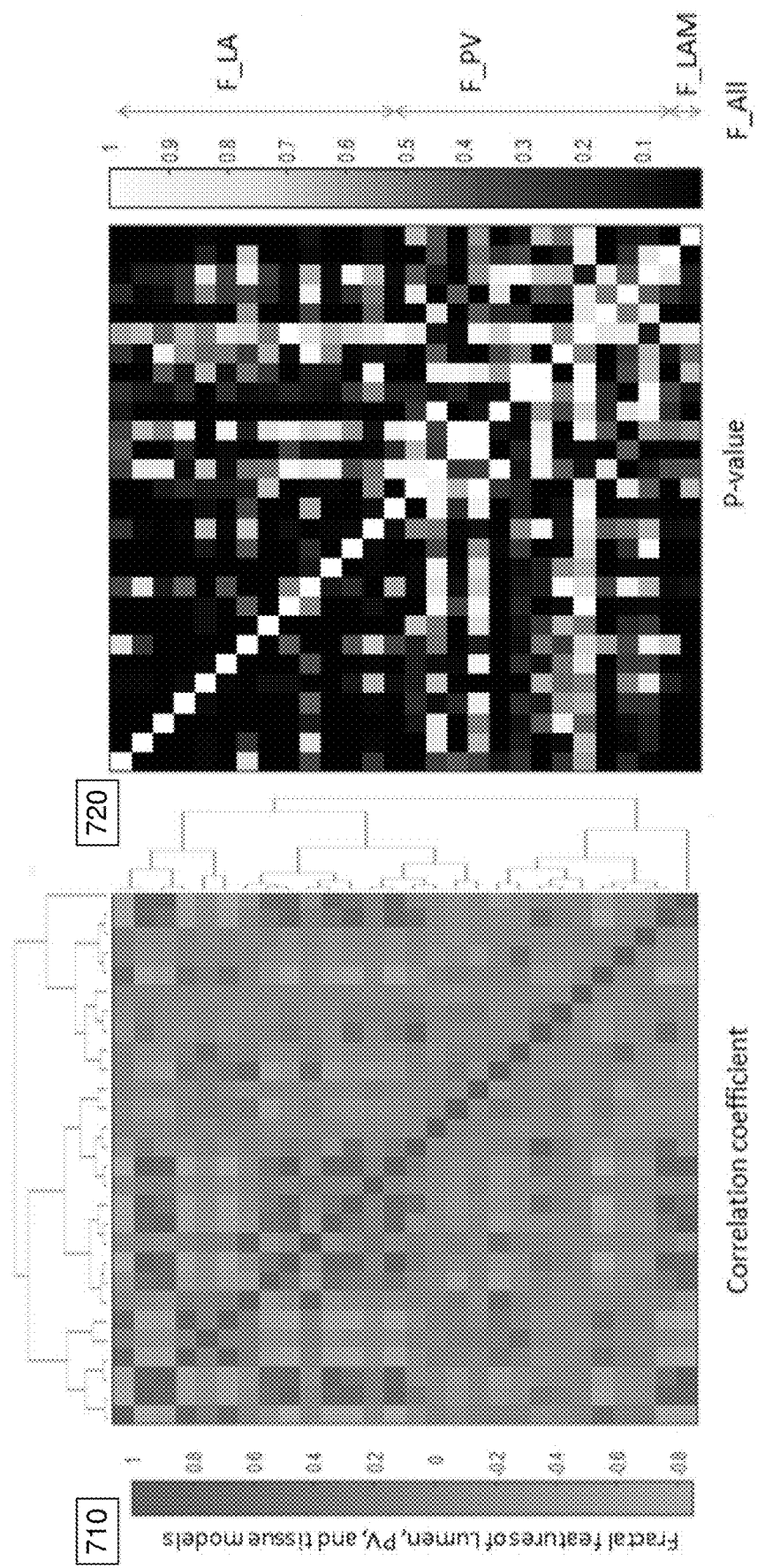
FIG. 7 illustrates correlation heat maps of features and p-values of all 28 fractal-based radiomic features of the first example use case, in connection with various aspects discussed herein.

Of the 26 shape-based fractal features evaluated for models $C_{PV}$ and $C_{LA}$ and two texture-based features for the tissue model or ($C_{LAM}$), Wilcoxon rank-sum testing was used to identify those features that were statistically significantly different (p<0.001). Referring to FIG. 7, illustrated are correlation heat maps of features (710) and p-values (720) of all 28 fractal-based radiomic features of the first example use case, in connection with various aspects discussed herein. A total of 28 features were extracted from $C_{AII}$ (n=137). Across all patients, each feature was individually compared with all other features, thereby generating correlation coefficients ($R^2$) and p-value. At 710, individual features were then clustered and plotted along both axes from F1-F28, and R is shown as a heat map, with areas of high correlation ($R^2>0.95$) shown in pink. Distributions into two subgroups are shown by cluster analysis, and the y-axis represents Euclidian distance from center of each cluster. 720 shows p-values of fractal features as a heat map. As illustrated in FIG. 7, the correlation between 28 fractal features was estimated to identify potential feature redundancy. The heat maps show that features relating to the PV and LA are correlated. Fractal features relating to PV were identified as the most discriminative features to predict AF recurrence.

Figure 8:
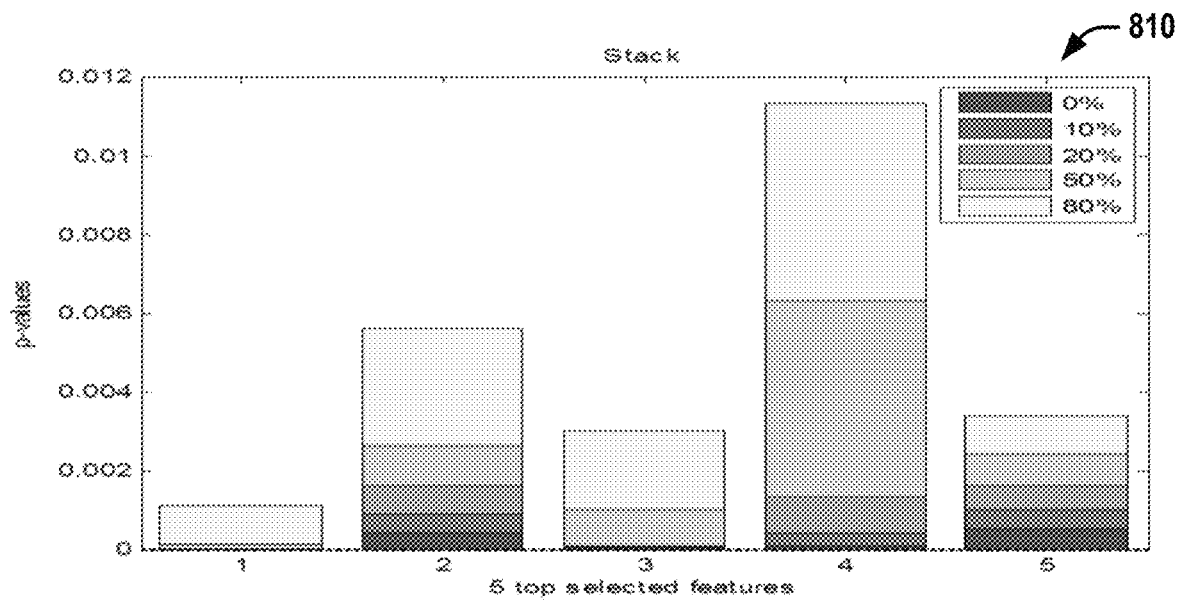
FIG. 8 illustrates charts showing p-values for five 3D fractal features for the $C_{AII}$ model and ROC curves for the $C_{AII}$ model following introduction of Gaussian noise, in connection with various aspects discussed herein.
Figure 8:
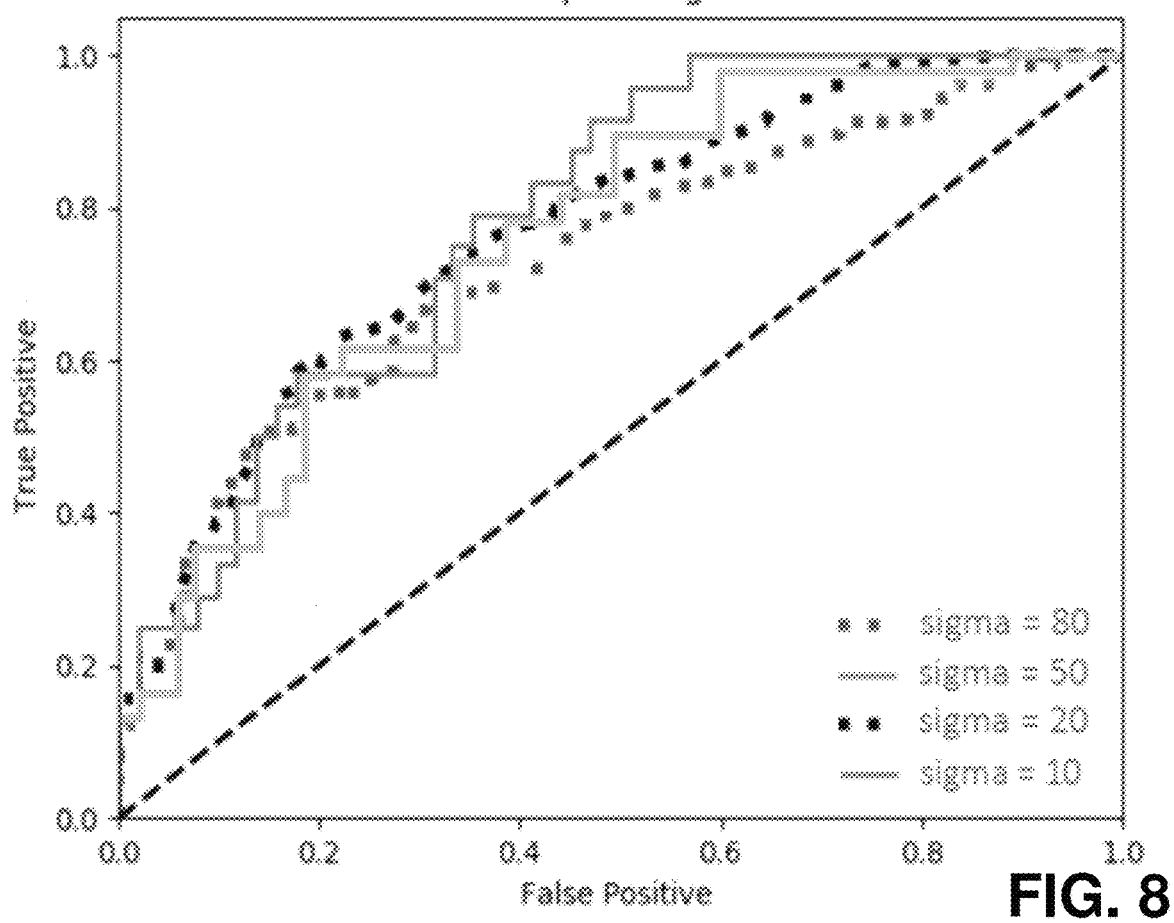

Referring to FIG. 8, illustrated are charts showing p-values for five 3D fractal features for the $C_{AII}$ model (810) and ROC curves for the $C_{AII}$ model (820) following introduction of Gaussian noise, in connection with various aspects discussed herein. Increasing the degree of introduced Gaussian noise (from $\sigma=10$ to $\sigma=80$), resulted in a corresponding reduction in the AUC of CAII from 0.81 to 0.75 as can be seen at 820. In general, it was found that the 3D fractal features were more robust to noise compared to the corresponding 2D fractal features. As illustrated in FIG. 8, the 3D fractal features appeared to be relatively stable for noise levels up to $\sigma=80$, yielding statistically significant separation between the AF+ and AF- patient groups. Features from the original masks were compared to segmentation masks of the different cardiac compartments and structures with varying noise levels. Shape descriptors of LA body and texture feature of CT scans were less affected by noise than shape descriptors of PVs. These findings appear to suggest that the introduced noise appears to have the greatest impact on the resulting 3D fractal features of the PV compared to the LA.

Experiment 2: A Fractal-Based Machine Learning Classifier to Predict AF Recurrence The objective of experiment 2 was to develop and test a machine learning classifier to predict AF recurrence post-ablation using fractal eatures.

On $D_1$, the model $C_{PV}$ had best prediction (AUC 0.78) with the 4 top selected features (median of 3D FD, Mean of 2D FD, entropy, and Gaussian mixture model of state space reconstruction), followed by the $C_{LA}$ (AUC 0.70) with the 4 top selected features (median of 3D FD, Mean of 2D FD, entropy, and Gaussian mixture model of state space reconstruction), as shown in Table 4.

The AUC for CPV alone was 0.72 with the 4 top selected features, including 3D FD of shape, entropy, Gaussian mixture model, and 2D FD of shape. $C_{AII}$ yielded an AUC of 0.81 with features corresponding to median of 3D FD of Lumen and PV, mean of 2D FD, and entropy. The ROC curves for model $C_{AII}$ trained on Di and tested on D2 are shown at 820. Atrial volume extracted with the toolbox SPM 12 from the individual segmentations of the LA was used to predict AF recurrence, based off a previously described approach. The AUC of the model using atrial volume was 0.59.

Figure 9:
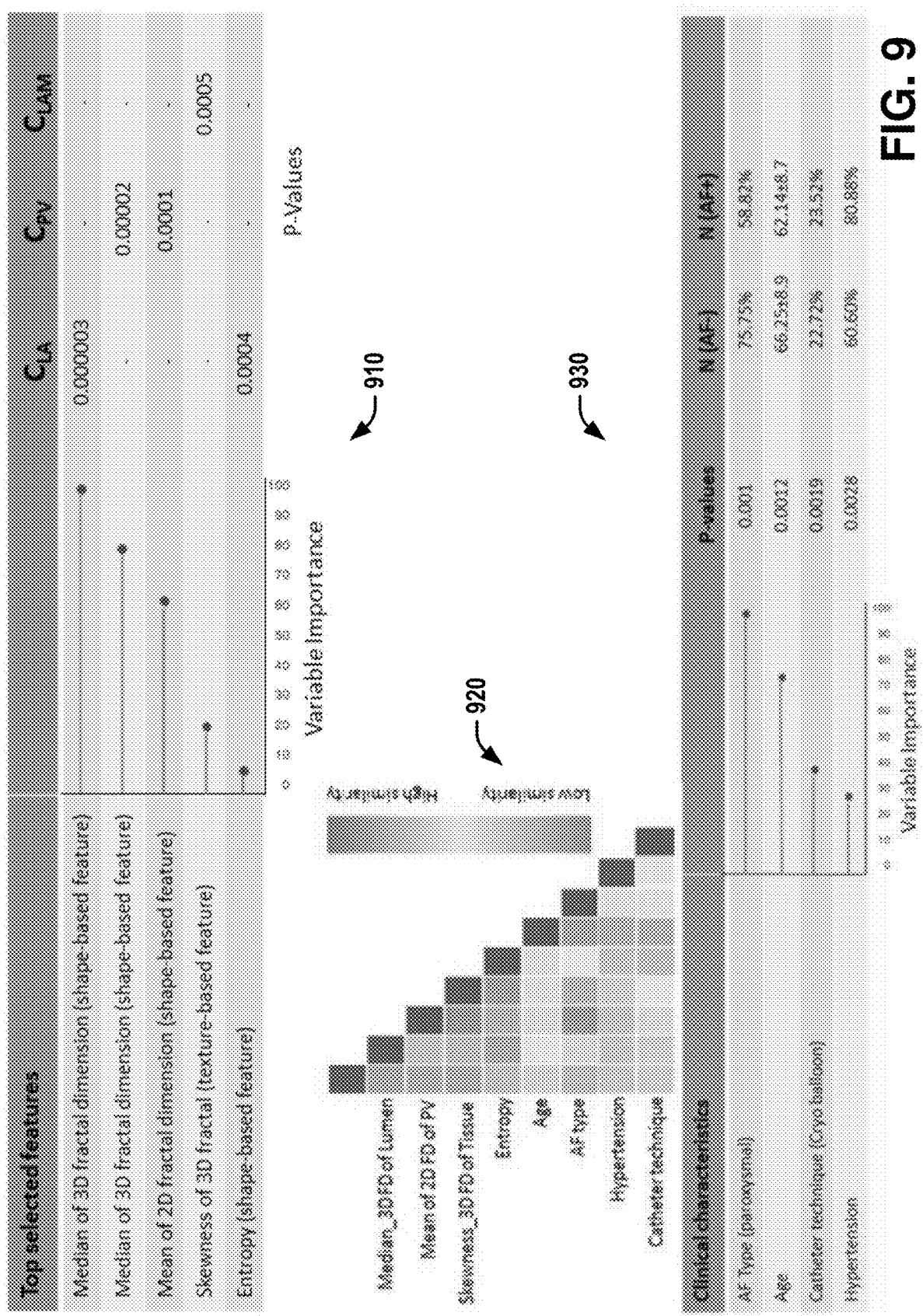
FIG. 9 illustrates charts showing the top fractal features, clinical features, and similarity between those features, in connection with various aspects discussed herein.

Referring to FIG. 9, illustrated are charts showing the top fractal features (910), clinical features (930), and similarity between those features (920), in connection with various aspects discussed herein.

At 910 is a chart showing the top 5 from 28 extracted fractal features, identified by variable importance ranking that were included within $C_{AII}$, with corresponding p-values. The top 5 ranked features comprised 4 fractal features of LA and PVs and 1 fractal texture feature. Also at 910 are the corresponding p-values for the individual 5 features in discriminating AF+ from AF- patients in Di when embedded into $C_{LA}$, $C_{PV}$ and $C_{LAM}$ respectively.

910 illustrates the p-values for the 5 top selected fractal features based off variable ranking importance. The top discriminating features for each of these individual models are also illustrated in 910. The results show that the 3D shape-based features of $C_{LA}$ and $C_{PV}$ and 3D texture-based features of $C_{LAM}$ were found to be discriminating.

Experiment 3: Integrating Fractal Features with the Clinical Variables and Evaluating Effect of Ablation and AF Type The objective of the third experiment was to assess whether fractal-based imaging features added predictive value beyond common clinical parameters that are associated with AF recurrence: age, LA volume, sinus rhythm at time of ablation, AF type, and catheter technique.

Referring again to FIGS. 9, 930 and 920 show feature selection and the relationship between clinical and fractal features on $D_1$ for $C_{AII}$, respectively. 920 shows the correlation map of the fractal features and clinical features. 930 shows reported clinical characteristics of $D_1$ based on AUC and the corresponding p-value of each feature of $C_{AII}$. The first column consists of p-values of each clinical characteristic. The second and third columns consist of number of patients or mean and variance of ages with AF- and AF+ respectively. The clinical variables were used to train model with D1 (n=137) and test the model with independent validation $D_2$. The model $C_{clin}$ yielded an AUC on the test data of 0.70 and the corresponding model for all fractal features $C_{AII}$, had an AUC of 0.81. The AUC for $C_{clin+FD}$ was 0.87 on $D_2$. Clinical features that were significantly associated with recurrence of AF are shown at 930.

Although the fractal features improve the prediction performance of $C_{clin}$, the correlation map between the clinical factors and the FD features were not found to be significant, as shown in the heat map at 920, further supporting the concept that FD features represent structural content and predictive value beyond clinical parameters, including LA volume and persistent AF, the main clinical factors previously reported to predict AF ablation success. In 920 and 930, all clinical features with p-values were considered and variable importance ranking to determine the discriminative features for prediction. The heat map and the plot show the 4 top selected features for $C_{Clin}$ and 5 top selected features of $C_{AII}$. The heat map suggests that AF type is correlated with the fractal dimension of CPV, Hypertension and catheter technique are correlated with entropy. The results of the variable importance feature selection appear to suggest that AF type is a significant factor for predicting AF recurrence. Using the trained model with catheter technique and fractal features of $C_{AII}$, the AUC was 0.84, while using AF type and $C_{AII}$, the corresponding AUC was 0.80. Table 5 shows the mean values for the top 5 fractal features in AF+ and AF- patients in $D_1$.

TABLE 5

The mean values of 5 top fractal features in
AF+ and AF− patients for $D_1$

| Top Selected Features | AF+ | AF− |
|---|---|---|
| F8: Median of 3D fractal dimension (LA model) (shape-based feature) | 3.5166 | 3.3245 |
| F21: Median of 3D fractal dimension (PV model) (shape-based feature) | 3.7401 | 3.590 |
| F14: Mean of 2D fractal dimension (shape-based feature) | 1.5894 | 1.4568 |
| F28: Skewness of 3D fractal (texture-based feature) | 0.1439 | 0.11604 |
| F10: Entropy (shape-based feature) | 0.5643 | 0.2605 |

Discussion

AF is a highly prevalent condition with substantial morbidity and mortality [43]. AF leads to complex changes in the LA, PVs, and LA wall that may contribute to AF recurrence. Characterization of the anatomy, geometry, and function of the LA with imaging techniques may help to understand the pathophysiological factors underlying this arrhythmia. Cardiovascular imaging technologies such as cardiac CT and cardiac magnetic resonance (CMR) imaging, continue to enhance the understanding of AF risk factors and natural history and identify patients at the highest risk for adverse outcomes. Several features of remodeling have been proposed as markers of the LA and PVs to predict AF recurrence after catheter ablation. Image-based approaches have been previously proposed to assess the likelihood of AF recurrence post ablation. These approaches have included ones focused on remodeling of LA with measures of atrial dilation, using metrics such as the anterior-posterior (AP) radius and atrial volume. AP radius predicted AF recurrence at 12 months post-ablation in CMR scans of the LA in over 100 AF patients; LA volume predicted AF recurrence at 1.5 years or 6 months post-ablation. Left atrial sphericity, a size-independent measure of how closely the LA body resembles a sphere was shown to be associated with recurrent AF to either LA volume or AP radius. The LA shape of a cohort of AF patients has been extracted using smooth (cubic Hermite) meshes. The vertical asymmetry is a shape metric to characterize morphological changes of the LA from MRI scans, attributes which may help differentiate between recurrent and non-recurrent patient populations. The features found to be most predictive of recurrence at both 12 and 24 months post-ablation included the LA shape predictor (AUC=0.71 and 0.68, respectively). Vertical asymmetry of the imbalance of size along the anterior to posterior direction between the superior and inferior left atrial has also been shown to be associated with post-ablation AF recurrence at 12 and 24 months. The LA shape can predict outcome independent of clinical factors from MRI scans. However, almost all of these approaches were focused on qualitative assessment of LA.

The first example use case used fractal analysis to represent shape and texture-based features in different dimensions (1D, 2D, and 3D) on CT scans. Fractal dimension of $C_{LA}$ and $C_{PV}$ was extracted on segmented masks to assess shape variations of LA and PVs. Also, 3D fractal dimension of the LA wall or $C_{LAM}$ was extracted to assess texture changes on CT scans. This work identified a set of quantitative fractal-based features that characterized the morphology and cardiac structure of the LA and PVs and texture changes of the LA wall that associated with the likelihood of developing AF. The first example use case comprised 3 principal experiments which were focused on discriminative fractal features of LA, classification, and integrating fractal features with the clinical variables.

Experiment 1 focused on identifying those fractal features that best discriminate patients who had AF recurrence from those who did not. Fractal features corresponding to the LA body and PVs on segmented masks and the texture variation of the atrial wall were identified as the most discriminating features. In experiment 2, on the test set D2, the model $C_{AII}$ was identified as being most predictive of AF recurrence. Previous studies on the relationship between the anatomical structure of the PVs and LA and the occurrence and development of AF have mainly focused on anatomical variations of PVs and LA. In one study, measurements of pulmonary vein ostia were performed by CT, resulting in different numbers and positions of pulmonary veins, with poor correlation of diameter measurements among the imaging modalities. Patients with the highest cross-sectional areas measured by CMR tend to have recurrent AF after ablation independently of the type of AF and LA size. Furthermore, it seems that preservation of pulmonary vein contraction on follow-up CMR might be an independent predictor of incomplete ablation. Another group demonstrated a relationship between PV structural characteristics and LA left atrial diameter with AF recurrence. That study reported that enlargement of LA is an independent risk factor for post-ablation recurrence of AF.

Experiment 3 explored the effect of clinical and procedural variables on likelihood of recurrence and investigated the role of radiomic features as a function of AF type and catheter technique. Clinically features previously predictive of recurrence are persistent AF and hypertension; here clinical models perform similarly to previous clinical predictive models of AF recurrence. Radiomic features were not strongly correlated with catheter type, suggesting that cardiac morphology may be an independent inherent predictor of recurrence rather than an artifact of procedure-specific anatomic challenges. The thickness of the atrium may have an important role in the non-invasive assessment of atrial structure. In combination with atrial tissue characterization, a comprehensive assessment of the atrial dimensions may allow prediction of atrial electrophysiological behavior. Another group found that heterogeneity in the left atrial wall thickness contributes to AF recurrence after catheter ablation. It was found that the 3D fractal dimension assesses heterogeneity in the left atrial wall that characterizes texture variations. The results suggest that the shape-based features of $C_{LA}$ and $C_{PV}$ and texture-based feature of atrial wall were most significant in predicting AF recurrence. Recent studies have been shown that the LA wall thickness in patients with persistent AF is lower than that of patients with paroxysmal AF; based on fractal analysis, the AF type is highly correlated with 3D texture features of atrial wall as shown in FIG. 9 at 920-930. The fractal feature based model was found to significantly outperform the model based off LA volume in predicting AF recurrence.

The fractal features improve the prediction performance of $C_{Clin}$; the correlation map between the clinical factors and the FD features were not found to be significant, as shown in the heat map in FIG. 9 at 920, further supporting the concept that FD features represent structural content and predictive value beyond clinical parameters, including LA volume and persistent AF, the main clinical factors previously reported to predict AF ablation success. The analyses also showed fractal features outperformed LA volume model, which had an AUC of only 0.59. FD features represent structural content and predictive value beyond clinical parameters, including LA volume and persistent AF.

Conditions

The first example use case had a limited sample size with a single center design and retrospective data assessment. Even though independent validation cases were used, all the scans came from a single site, without multisite validation explicitly establishing the generalizability of the approach. While an evaluation of the sensitivity of the approach to segmentation performance was done, the first example use case did not explicitly address or evaluate the sensitivity of the approach to different CT slice thicknesses, reconstruction kernels and scanners. LA fibrosis by late gadolinium enhancement has also been shown to be important factors in arrhythmia and patient stratification by CMR algorithms, which cannot be used on CT scans, though it is possible that textural differences on fractal CT analyses could be detecting similar substrates. Despite these conditions, the first example use case presented a new fractal-based approach that appears to provide independent prognostic value based on shape and textural measurements of LA, PVs, and LA wall in predicting AF recurrence.

Conclusions

Fractal analysis of 3D morphology of the left atrium and pulmonary veins from CT scans were found to be predictive of AF recurrence following catheter ablation and may provide utility in improving patient selection for AF ablation. Various embodiments can also employ similar techniques in determining follow-up needs for AF risk after ablation. The type of AF (paroxysmal vs. persistent) is highly correlated with 3D texture features of $C_{LAM}$. Beyond type of AF, however, fractal analyses provided significantly improved prediction performance over clinical features, supporting the concept that FD features represent structural content and predictive value beyond clinical features, including LA volume and AF persistence.

Example Use Case 2: Prediction of Atrial Fibrillation Recurrence Post-Ablation using Machine Learning Derived Fractal Analysis from CT (Computerized Tomography) Scans The following discussion provides example embodiments in connection with a second example use case involving training, validation, and testing of machine learning models to predict recurrence of atrial fibrillation based at least in part on fractal features.

Overview: Previous studies showed that the left atrial (LA) remodeling may predict recurrence after catheter ablation of atrial fibrillation. For the second example use case, it was hypothesized that fractal analysis can be used to assess the morphological changes of LA for prediction.

Purpose: To develop a fractal-based classifier for predicting risk of post-ablation AF recurrence on CT scans for quantitative characterization of the left atrium and PVs on CT scans.

Materials and Methods: The second example use case was comprised of pre-ablation contrast CT scans from 350 AF patients who underwent ablation. AF recurrence was defined at 3 months to 1 year. Fractal-based features were used to quantify morphological variations within left atrium and pulmonary veins for prediction of AF recurrence. The LA region was segmented using syngo.via (Siemens) software, including lumen, PV, and tissue models. Fractal dimension and chaos-based features were extracted from these models of each patient to create descriptors for prediction. A random forest classifier was used to train the model with 150 patients with extracted features and seven clinical parameters. To validate the fractal-based classifier, an independent test set of N=200 patients was used.

Results: Statistically significant differences were observed for fractal analysis of Lumen, PV, Tissue models, distinguishing between AF+ and AF− (p<0.001). Using the 5 top selected features, the PV model had the best prediction (AUC 0.81), followed by the Lumen model (AUC 0.73), and the myocardial tissue model (AUC 0.63). The AUC of the combination model was 0.85.

Conclusion: Fractal analysis can represent morphological characteristics of the left atrium and pulmonary veins on CT scans, which may be useful in predicting recurrence of AF post-ablation. Fractal and clinical features improve the prediction performance of AF recurrence. The performance of the combination model of Lumen, PV, and Tissue models using fractal-based features was better than the model based on clinical parameters, while the trained model using clinical and fractal features were best on independent dataset.

Abbreviations: AF (Atrial Fibrillation), LA (Left Atrium), PV (Pulmonary Vein(s)), FD (Fractal Dimension), AF+ (Patient(s) who had post-ablation recurrence), AF− (Patient(s) who did not have post-ablation recurrence), ROC (Receiver Operating Characteristic Curve), AUC (Area Under the (ROC) Curve).

Summary: The second example use case investigated the variation of remodeling patterns in different parts of Lumen, PV, and tissue models. The FD of pulmonary veins can represent rich information to characterize morphological changes of the LA for prediction. 2D, 3D fractal analysis, and chaos-based features with (P<0.001) were associated with atrial fibrillation recurrence. An independent dataset was used for validation with AUC>0.78 in predicting AF recurrence.

Overview

Atrial Fibrillation (AF) is a common cardiac arrhythmia that affects 1-2% of the population in which rapid and irregular electrical atrial activation causes loss of synchronized contractions of the atria. AF is predicted to affect 6-12 million people in the USA by 2050 and 17.9 million in Europe by 2060. AF is associated with significant morbidity, including increased risk of stroke, heart failure and death. AF consumes significant health resources and is associated with a fourfold to fivefold increased risk of thromboembolic events. Among patients who experience strokes, AF is associated with 1.5% of strokes at 50 years of age and 23.5% at 80 years. Although catheter ablation is an invasive technique to treat AF with pulmonary vein (PV) isolation, AF recurrence rates after ablation are high, indicating a need for improved prediction of AF recurrence and ablation targets.

AF induces morphological changes of the left atrium (LA), which manifest as changes in atrial volume, shape, the atrial wall, and PVs. The structural changes could be used to predict AF recurrence using computed tomography (CT) and magnetic resonance imaging (MRI) scans. MRI has been promoted to yield information on putative LA scarring that is being targeted for ablation in a clinical trial. Several models have been proposed to predict AF recurrence after ablation using clinical features such as age, hypertension, persistence of AF and LA scarring. Further investigation into the different LA morphologies associated with AF recurrence may support the use of imaging in identifying patients for ablation. However, the approach remains difficult to reproduce and controversial.

Currently there are no validated biomarkers for early identification of those patients that are likely to fail ablative therapy for AF. The focus of the second example use case was to develop and validate a novel machine learning (ML) and computational imaging approach to identify fractal analysis of LA on pre-treatment CT scans that are associated with increased likelihood of risk of AF recurrence. The second example use case identified a set of quantitative fractal-based and chaos-based descriptors for subtle characterization of morphology and cardiac structure of the LA and PVs and their association with the likelihood of developing AF, as well as potentially identifying additional ablation targets.

Materials and Methods

Patients

Pre-ablation contrast CT scans were obtained from 350 patients undergoing AF ablation at the Cleveland Clinic. 150 patients were used for training, and the model was validated using 200 patients. The Lumen, PV, and tissue are segmented from CT scans using syngo.via (Siemens) software at Cleveland Clinic, including LA Lumen, PV, and Tissue models. Table 6 provides a description of models associated with the second example use case.

TABLE 6

Descriptions of Models

| Model | Description |
| --- | --- |
| Lumen model | Comprises the left atrium body and the ostia of the PVs |
| PV model | Comprises the LA lumen and the full structure of PVs visible on CT |
| Tissue model | The LA myocardial tissue model comprises the LA wall |

Figure 10:
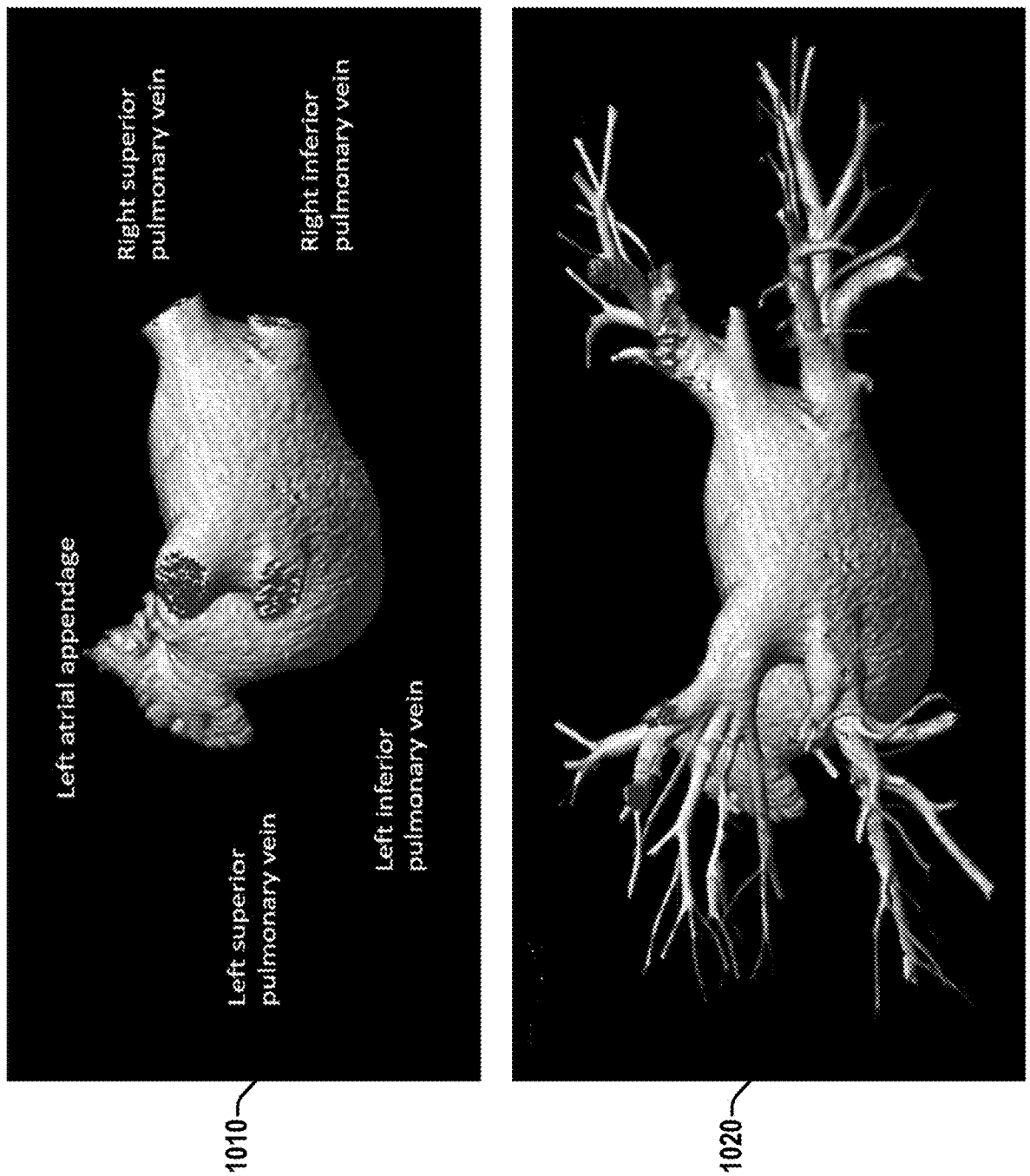
FIG. 10 illustrates example images showing the left atrium (LA) lumen model and the pulmonary vein model, in connection with various aspects discussed herein.

Referring to FIG. 10, illustrated are example images showing the LA lumen model (1010) and the PV model (1020), in connection with various aspects discussed herein.

The new classes of computationally derived image features from CT to predict AF recurrence.

For the second example use case, it was hypothesized that the computer-extracted fractal features relating to the shape of the LAA and the PVs from routine CT scans, in conjunction with key clinical factors, will be associated with risk of recurrence in post-ablation AF patients. Fractal dimension analysis is a mathematical technique that provides an excellent explanation of the ruggedness of natural surfaces and many other natural phenomena. Fractal analysis characterizes the heterogeneity and complexity of an object in an image. The second example use case sought to look at the additive benefit of these fractal features of the PV and the lumen to better predict which patients are likely to have recurrence of AF post-ablation and to determine anatomic features contributing to differences.

For the second example use case, a ML approach was developed to predict AF recurrence using fractal analysis to characterize morphological changes of LA. The morphological changes of LA, PVs, LAA, and the LA wall were integrated with clinical features to identify a predictive model for AF recurrence. The second example use case combined fractal analysis and chaos-based features of LA, PVs, and LA wall for predicting AF recurrence. The fractal analysis of LA can lead towards positively transforming the current clinical workflow via a non-invasive, safe, and effective mechanism for prediction AF recurrence, and possibly for ablation targeting. To assess morphological changes in different parts of LA, fractal features were extracted, including 2D, 3D fractal dimension, and chaos-based features from CT scans and binary masks. The top fractal features from LA that maximally distinguish AF recurrence and non-recurrence were identified via feature selection and then used to train machine learning classifiers (e.g., Support Vector Machine(s) (SVM(s)) and Random Forest).

Assessing Sensitivity of Fractal Features and Classifiers to Type of Ablation and Clinical Parameters.

The performance of clinical parameters associated with AF recurrence was compared against the radiomic features. These parameters included age, sex, left atrial volume (LAV), left ventricular ejection fraction (LVEF), body mass index (BMI), sinus rhythm at the time of ablation, and AF type, clinical factors that have been reported to be predictive of AF ablation success. The classifier was trained using the clinical features and fractal features to assess sensitivity of the features and classifiers to type of ablation and clinical parameters. The method can improve the prognostic and predictive performance of AF recurrence.

Results

The cohort used in the study consisted of 119 patients, with 67 having recurrence of AF and 52 not having recurrence within 3 months-1 year of ablation. The details of the datasets for training and testing are in Table 7.

TABLE 7

Dataset Description

| Datasets | # patients | Used data |
| --- | --- | --- |
| Training set | 150 | 67 AF+ and 52 AF− |
| Test set | 200 | 20 AF+ and 46 AF− |

Experiment 1: In texture analysis, to determine the important aspects of the complexity of a structure not revealed by classical morphometry based on Euclidean geometry, fractal analysis can be used. Fractal dimension analysis is a mathematical technique that provides an excellent explanation of the ruggedness of natural surfaces and many other natural phenomena. In the field of medicine, fractal analysis has been applied to pathology, anatomy, and medical imaging.

Fractal analysis characterizes textures, contours, shapes, and the heterogeneity and complexity of objects in image. In the second example use case, fractal analysis and chaos-based features were extracted from binary masks and CT scans of the Lumen, PV, and tissue models. The fractal dimension was measured from binary masks and CT scans of the Lumen, PV, and tissue models. The 2D fractal dimension was measured from each slice of binary masks using box-counting method. 3D fractal analysis was used with a spectral density depending on three frequencies corresponding to x, y, and z directions from binary masks of Lumen and PV models.

Figure 11:
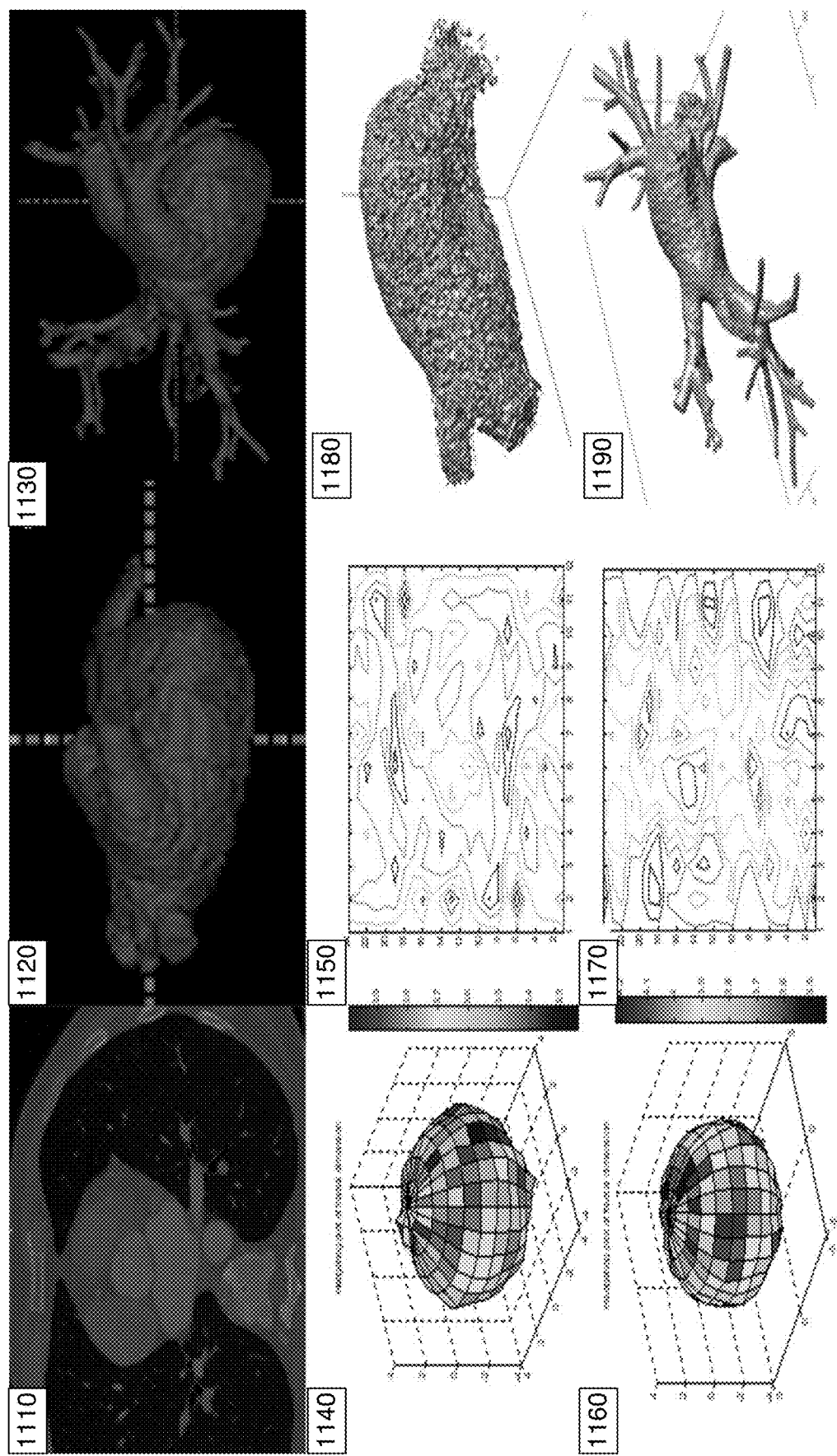
FIG. 11 illustrates example images and plots showing fractal analysis of binary and CT scans, in connection with various embodiments discussed herein.

Referring to FIG. 11, illustrated are example images and plots showing fractal analysis of binary and CT scans, in connection with various embodiments discussed herein. FIG. 4 shows: a CT scan at 1110, a binary mask of a Lumen model at 1120, a binary mask of a PV model at 1130, a Hedgehog plot of Lumen model for AF+ using 3D fractal analysis at 1140, a 2D view of 1140 at 1150, a Hedgehog plot of the Lumen model with AF− at 1160, a 2D view of 1160 at 1170, and 3D fractal analysis of the Lumen model and PV models from CT scans at 1180 and 1190, respectively.

As can be seen in the hedgehog plots of FIG. 11 (1140 and 1160), the shape of the hedgehog plot is a sensitive indicator to the degree and direction of anisotropy. The hedgehog plot of intercepts infers the degree of anisotropy. In an isotropic case, the plot of intercepts is nearly a sphere that decreases the fractal dimension of the mode.

Figure 12:
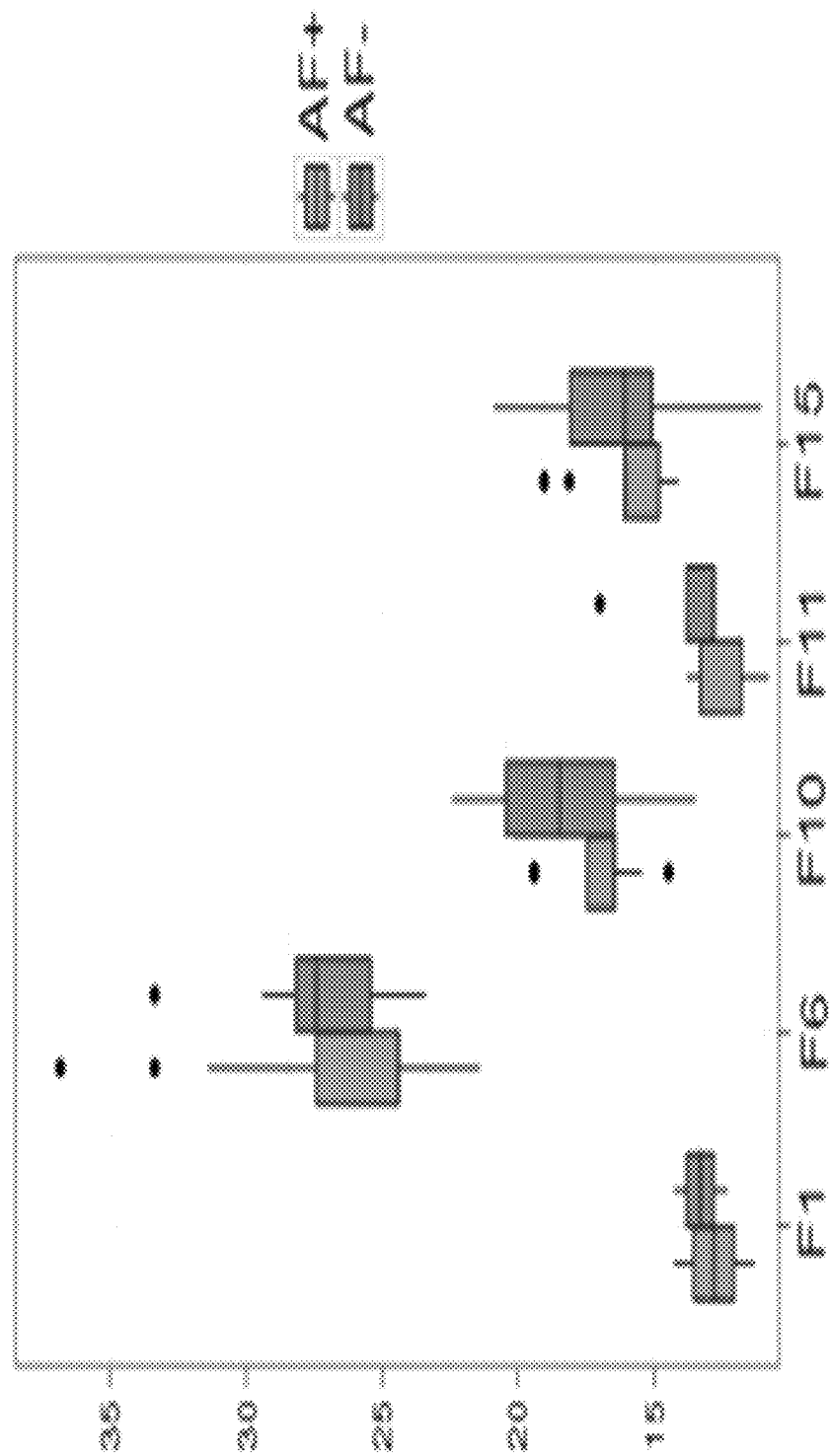
FIG. 12 illustrates a box plot shows the distribution of fractal dimensions in the first example use case, in connection with various aspects discussed herein.

Referring to FIG. 12, illustrated is a box plot shows the distribution of fractal dimensions in the second example use case, in connection with various aspects discussed herein. Five selected features using minimum redundancy maximum relevance (mRMR) are shown in FIG. 12, including F1, F6, F10, F11, and F15 with p-value p<0.001. The 3D fractal analysis of the LA can separate recurrence and non-recurrence with p-value p<0.001 as can be seen in FIG. 12. Greater values of fractal dimensions are reflective of greater levels of anatomic complexity and surface variation. Of the 15 fractal and chaos-based features evaluated in the second example use case, Wilcoxon rank-sum testing was used to identify those that were statistically significant (p<0.001). Five features were found to be significant and are shown in FIG. 12. As shown in FIG. 12, the boxplots of these features show that the fractal features may help to predict AF recurrence.

Figure 13:
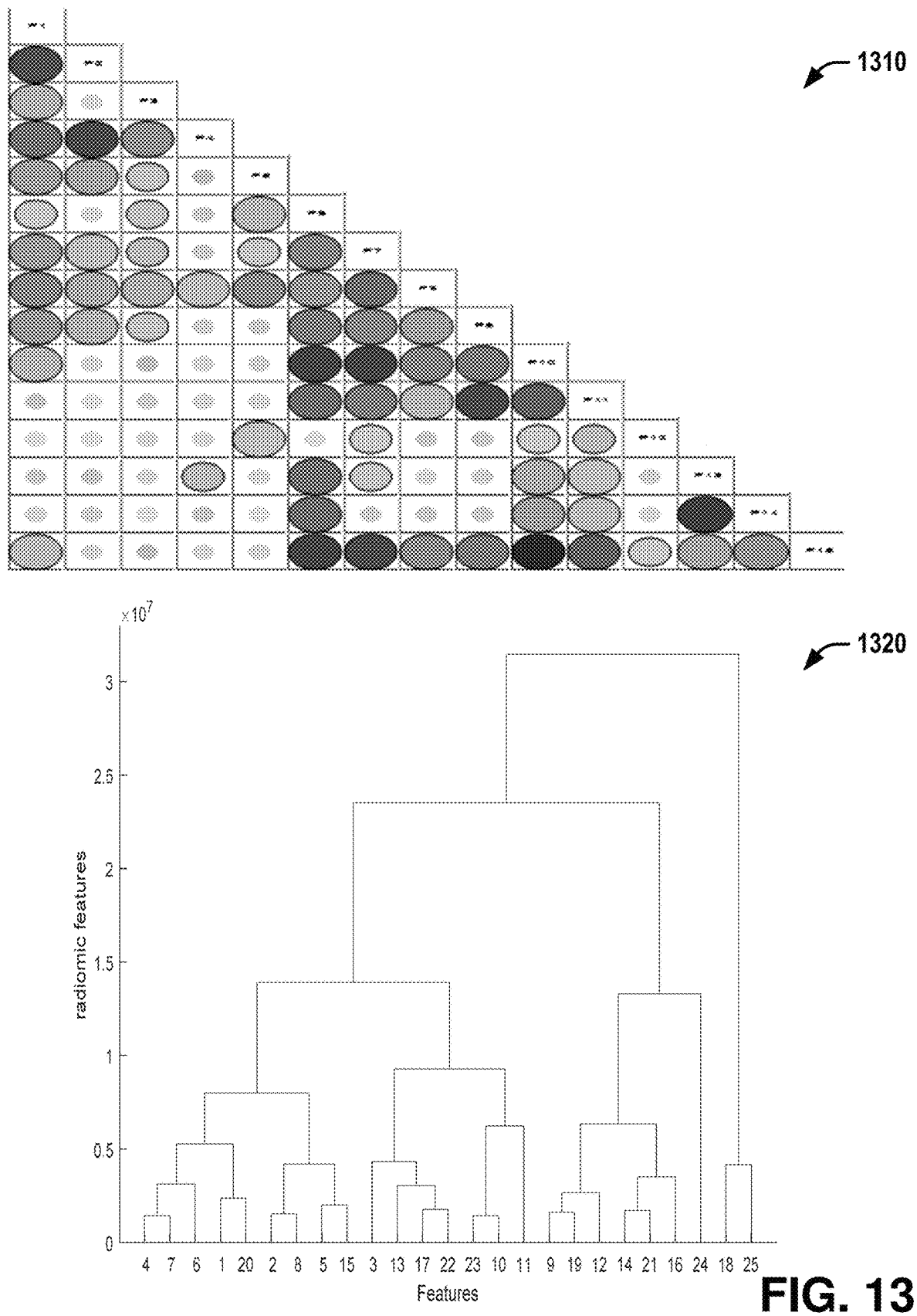
FIG. 13 illustrates a covariance matrix of fractal-based radiomic features along with a dendrogram, in connection with various aspects discussed herein.

Referring to FIG. 13, illustrated is a covariance matrix of fractal-based radiomic features (1310) along with a dendrogram (1320), in connection with various aspects discussed herein. A total of 15 features were extracted from the PV model of in 350 patients. Across all patients, each feature was individually compared with all other features by using regression analysis, thereby generating correlation coefficients ($R^2$) and p-value. As shown at 1310, individual features were then clustered and plotted along both axes from F1-F15, and R is shown as a heat map, with areas of high correlation ($R^2>0.95$) shown in red. Thus, each of the red squares along the diagonal contains a group of features that are highly correlated with one another and are thus redundant. Chart 1320 shows distributions into two subgroups as shown by cluster analysis and y-axis represents the fractal dimension. The dendrogram 1320 has only 25 leaf nodes using average clustering, and also shows the return mapping of the original data points to the leaf nodes shown in the plot.

As seen in FIG. 13, the 3D fractal analysis of CT represents rich information for prediction. Further analysis was performed within the group. The distribution of fractal dimension was assessed using the cluster analysis method. This analysis revealed a distribution into two distinct subgroups based on their fractal dimension. The cluster analysis of 3D fractal analysis is shown at 1320.

Table 8, below, shows details of radiomic fractal-based features employed in the second example use case.

TABLE 8

Details of Radiomic Fractal-Based Features

| Features | Details |
|---|---|
| 2D fractal feature of binary mask and CT scans | Box counting method is used to extract fractal dimension of each slice of binary mask. |
| 3D fractal of binary mask | Fractal dimension and intercept of a 3D volume along each radial line using Fourier analytical technique. |
| 3D fractal using spectral density function of CT scan | The fractal dimension image is generated by considering each pixel in the original CT image as a single fractal dimension estimated from its 7 × 7 neighbors. |
| State space reconstruction | Convert image to a time series and estimate optimal dimension and delay. |

Experiment 2: Validate fractal-based classifier developed using a test set 66 of 200 patients.

To evaluate prognostic and predictive performance of classifier using fractal features, an independent dataset was used to robustly validate the findings. Prediction performance can be quantified by AUC.

The cohort used in the study consisted of 66 patients. To assess morphological changes of different parts of LA, three models were considered for prediction (e.g., see Table 6).

In experiment 2, radiomic features extracted from the three models of LA were used to assess significant regions for AF recurrence prediction. A random forest classifier was used for a training step with 119 patients. For validation of the method, an independent dataset with 66 patients was used. 5 features for each model were selected using the principal component analysis (PCA) method. On the test set, the PV model had the best prediction (AUC 0.81), followed by the Lumen model (AUC 0.73), and the myocardial tissue model (AUC 0.63).

To reduce the redundancies of the PV and Lumen models, a model obtained with PV model without Lumen was used to assess the relationship of radiomic features and pulmonary veins. Then the 5 selected features were used for training the classifier. The AUC of the pulmonary veins was 0.74. The results show that the morphological changes of the pulmonary veins significantly more efficient than that of the Lumen model for AF recurrence prediction. A combination model obtained from the PV, Lumen, and Tissue was used for prediction. The AUC of the 5 significant features of the combination model was 0.85.

Figure 14:
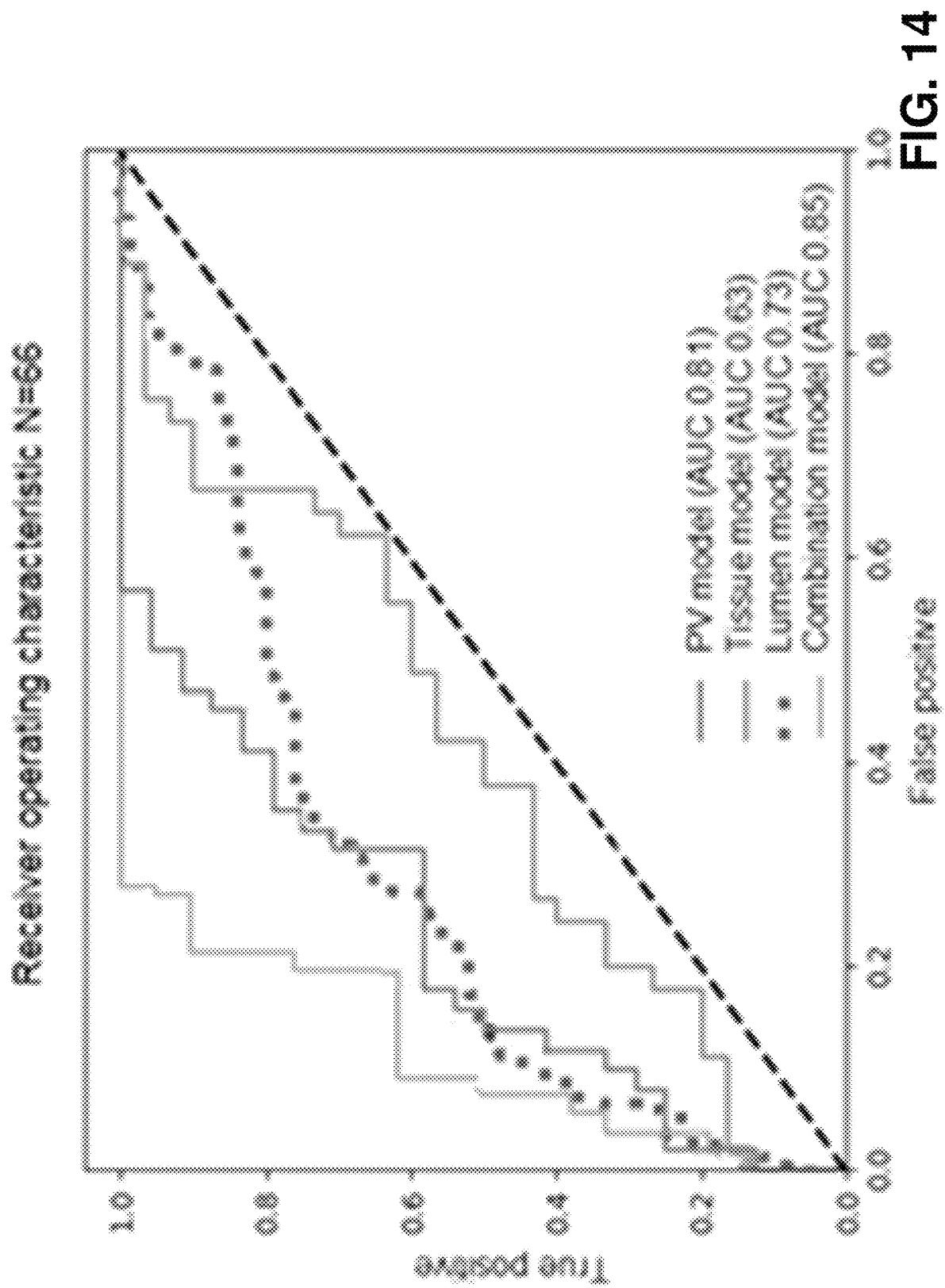
FIG. 14 illustrates a chart showing Receiver operating characteristic (ROC) curves of the fractal-based radiomic classifier trained on 150 patients, in connection with various aspects discussed herein.

Referring to FIG. 14, illustrated is a chart showing Receiver operating characteristic (ROC) curves of the fractal-based radiomic classifier trained on 150 patients, in connection with various aspects discussed herein. FIG. 14 shows ROC curves of trained models, including PV, Lumen, Tissue, and combination model tested on the independent test set with performance plotted on ROC space. The combination model performed statistically significantly better at recognizing patients with AF recurrence on the independent test set. The AUC for the prediction of AF recurrence was 0.85 for combination model. The combination model preserves a strong ability to predict AF recurrence using morphological changes of LA.

Experiment 3: Experiment 3 assessed the effects of AF type, ablation technique, and clinical characteristics and fractal features. The effect of AF type (paroxysmal, persistent) or catheter technique (cryoballoon, radiofrequency ablation, substrate ablation beyond PV isolation) to improve prediction of outcome was considered.

Clinical features that were significantly associated with recurrence of AF, from among 70 clinical features, are shown in table 9.

TABLE 9

Comparison of Clinical Characteristics by Recurrence of Atrial Fibrillation

| Characteristic | p-value |
|---|---|
| Age | 0.0011 |
| Sex | 0.051 |
| Left atrial volume (LAV) | 0.17 |
| Left ventricular ejection fraction (LVEF) | 0.006 |
| Body mass index (BMI) | 0.004 |
| Sinus rhythm | 0.003 |
| LA scarring | 0.0014 |
| Hypertension | 0.031 |

TABLE 9-continued

Comparison of Clinical Characteristics
by Recurrence of Atrial Fibrillation

| Characteristic | p-value |
|---|---|
| AF Type | 0.001 |
| Persistence of AF | 0.0002 |
| Catheter technique | 0.002 |

The performance of the clinical parameters associated with AF recurrence was compared against the fractal features. The fractal features extracted were evaluated against AF type and catheter technique using the results of Random forest classifier trained on the fractal and clinical factors. Of the 15 fractal features, Wilcoxon rank-sum testing was applied to determine statistically significant features with $p<0.001$. Five features were significant and selected for training as can be seen in FIG. 5.

The performance of the classifier was evaluated using AUC of independent dataset. Using clinical factors the AUC was 0.69 and using the fractal features the AUC was 0.85. The combination of the clinical and fractal features can improve the performance of classifier with AUC of 0.88. The clinical parameters considered are associated by ablation outcome with appropriate AF recurrence prediction.

Figure 15:
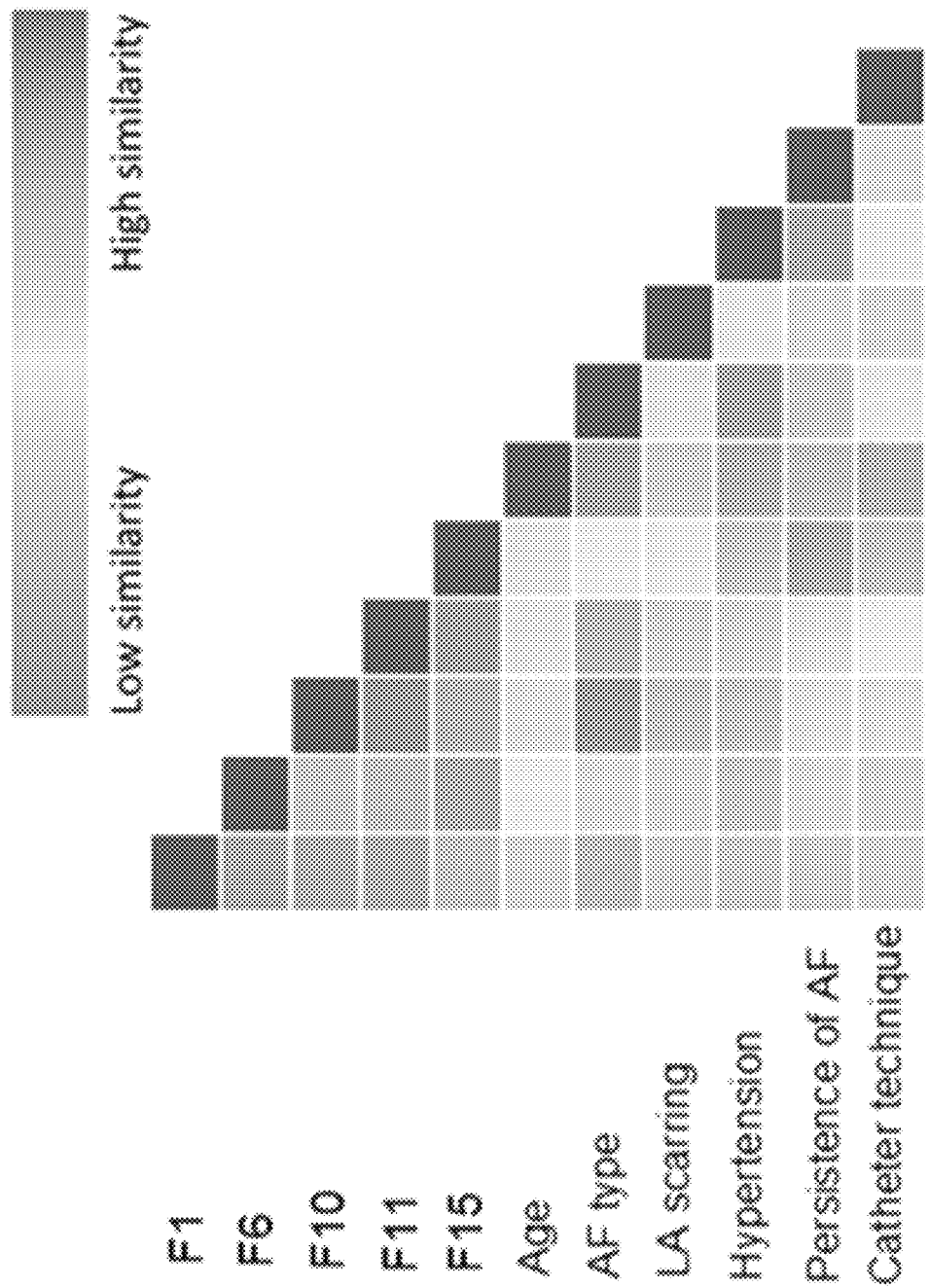
FIG. 15 illustrates a correlation map of the 5 selected radiomic features and 7 selected clinical features of the first example use case, in connection with various aspects discussed herein.

Referring to FIG. 15, illustrated is a correlation map of the 5 selected radiomic features and 7 selected clinical features of the second example use case, in connection with various aspects discussed herein. Although the fractal features can improve the prediction performance associated with clinical features, the correlation map between these factors and the fractal features are not significant, as shown in the heatmap in FIG. 15. The heatmap show that correlation between AF type and F10 and persistence of AF and F15 is significant.

The fractal analyses of different parts of LA have the potential to improve prediction of AF recurrence. Using the trained model with catheter technique using cryoballoon, the performance of prediction was AUC=0.87, and with radiofrequency ablation, substrate ablation beyond PV isolation, the AUC is the same as the combination model. For AF type, the result is the same.

Discussion

The second example use case could also be used in determining follow-up needs for AF risk after ablation, but importantly might also highlight anatomic areas such as PV, Lumen, and Tissue that may not otherwise be adequately targeted during routine ablation. Interestingly, earlier work associated with the second example use case highlighted certain areas around PV ostia and the LA appendage (LAA) as predictive of AF recurrence. Confirmation of such findings could lend more credence toward LAA isolation or focus on certain segments of PV ostia for additional isolation. Techniques employed in the second example use case can help enable precision cardiovascular medicine, advancing cost-effective, data-driven, and patient-specific clinical care. The second example use case established a machine learning-based radiomic analysis in clinical decision support, which could be applied to other challenges in cardiovascular medicine.

The atrial remodeling effect has inspired development of computer derived imaging and ML-based methods to characterize the LA variations for predicting post ablation recurrence. The second example use case identified a set of quantitative fractal descriptors for subtle characterization of morphology of the LA and PVs and their association with the likelihood of developing AF, as well as potentially identifying additional ablation targets.

Recent studies have shown that radiographic features of PV morphology from chest CT can predict risk of post-ablation AF. In the second example use case, the pulmonary vein and left atrial morphometry were used as a means of predicting response to PV isolation. Radiographic features were obtained characterizing LA size, PV morphology, and angle of vein entry into the LA with N=100. The results of the second example use case showed that combination of clinical features and radiographic features were effective in predicting recurrence using cross validation method as can be seen in Table 10.

TABLE 10

Results of Second example use case

| Methods | AUC |
|---|---|
| Radiographic features | 0.67 |
| Clinical features | 0.73 |
| Radiographic and clinical features | 0.75 |
| Shape features | 0.67 |
| Clinical features | 0.71 |
| Shape and clinical features | 0.78 |

Also, the second example use case introduced a new machine learning approach for predicting likelihood of recurrence using differences in atrial shape surrounding the PV ostia and the base of the LAA with N=68 patients using cross validation. The results of the method were reported in Table 10. However, these results have not yet been validated on an independent test set and have AUC<0.78.

The second example use case proposed fractal-based approaches and a fractal-based classifier showed improved performance for predicting of AF recurrence. In preliminary results, 3D fractal features characterizing LA and PV morphology could predict AF recurrence after ablation. The second example use case trained ML classifiers with N=119 and 7 features. On the test set with N=66 and 7 features, the PV model had best prediction (AUC=0.80), and followed by the LA volume model (AUC 0.75).

The second example use case extracted radiomic features from CT scans and binary masks from the LA lumen, PV, and LA tissue models. These features were combined with clinical parameters to improve the predictive and prognostic performance for AF recurrence. Additionally, a dependent dataset was used to validate the proposed model.

Example Use Case 3: Fractal Analysis of Left Atrium and Pulmonary Veins Predict Likelihood of Recurrence of Atrial Fibrillation Post-Ablation on CT The following discussion provides example embodiments in connection with a third example use case involving training, validation, and testing of machine learning models to predict recurrence of atrial fibrillation based at least in part on fractal features.

Purpose: Atrial fibrillation (AF) is an arrhythmia that affects 1-2% of the population and increases risk of stroke. Catheter ablation is a standard treatment, but AF recurs in 20-40% within a year after ablation, indicating a need for improved prediction of AF recurrence. Morphological characteristics of the left atrium (LA) and pulmonary veins (PVs) on CT scans may be predictive of AF recurrence. Variations within LA and PV anatomy can be characterized by fractal analysis. The purpose of the third example use case was to use fractal analysis to investigate the relationship between morphological characteristics of the LA and PVs with recurrence of AF post-ablation.

Materials and Methods: The third example use case was comprised of pre-ablation contrast CT scans from 152 AF patients who underwent ablation, including 75 with AF recurrence (AF+) and 77 without recurrence (AF−). AF recurrence was defined at 3 months to 1 year. Two segmentation models were created for each patient: a left atrial lumen model and a pulmonary vein model.

Figure 16:
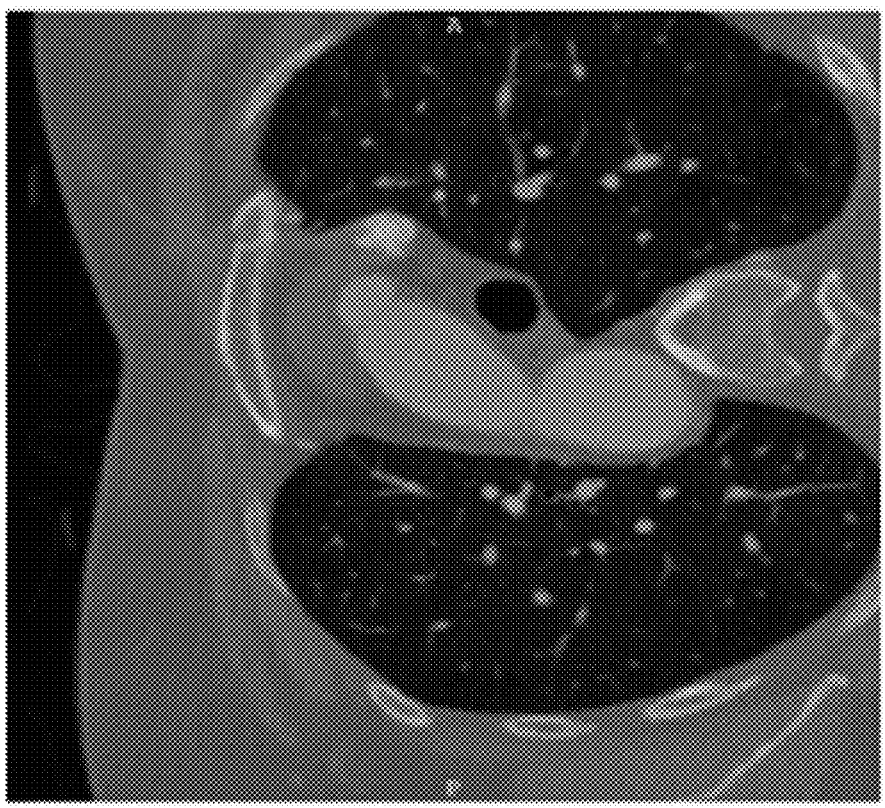
FIG. 16 illustrates example CT scans of an AF+ patient (top) and an AF− patient (bottom), in connection with various aspects discussed herein.
Figure 16:
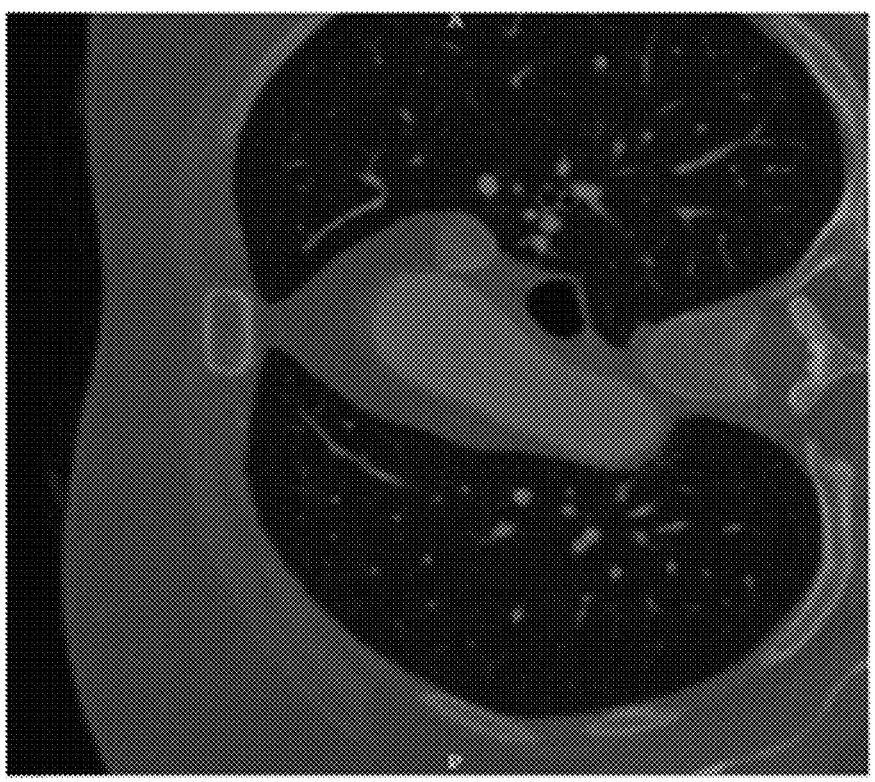
Figure 17:
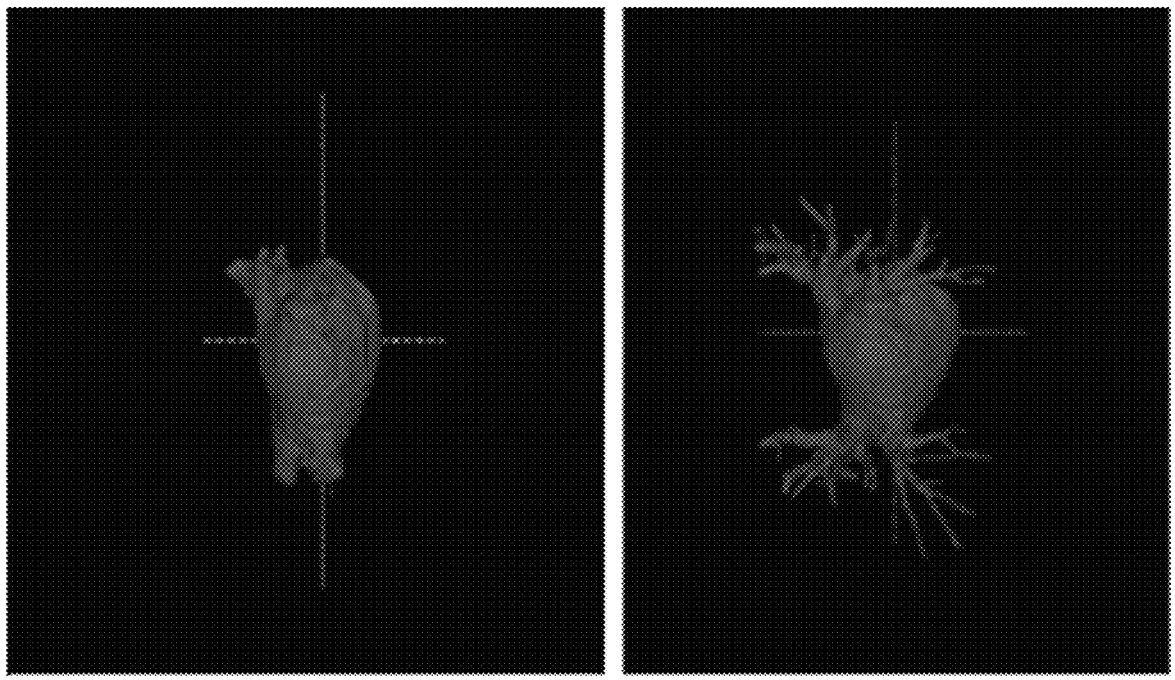
FIG. 17 illustrates example binary images of the CT scans of FIG. 9 based (AF+ in the left column and AF− in the right column) on two segmentation masks, the left atrial lumen model (top row) and PV model (bottom row), in connection with various aspects discussed herein.
Figure 17:
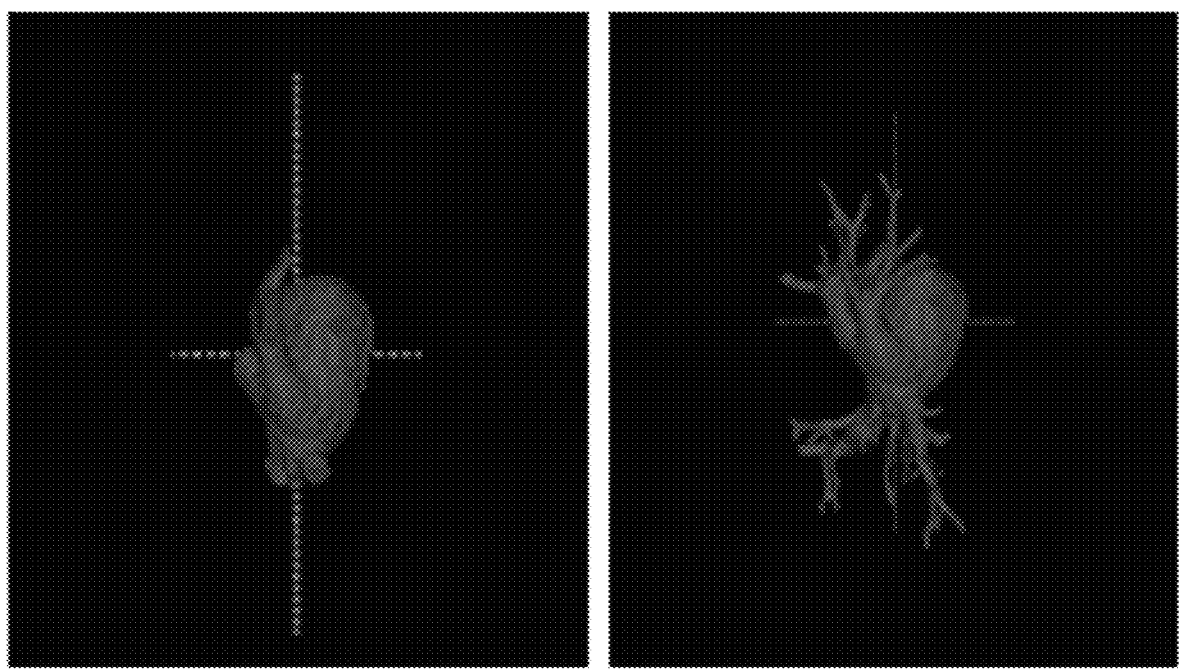
Figure 18:
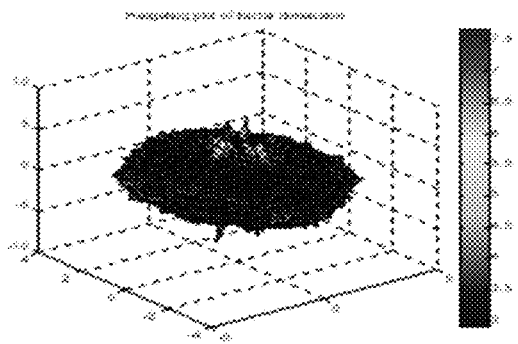
FIG. 18 illustrates charts showing 3D fractal analysis of lumen models for AF+ (top) and AF− (bottom), in connection with various aspects discussed herein.
Figure 18:
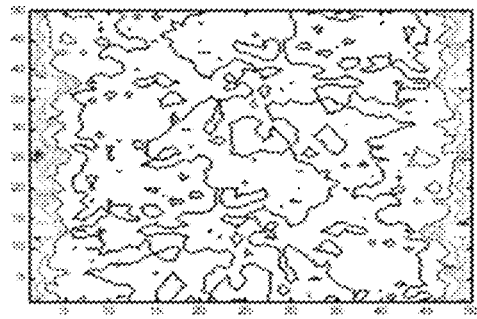
Figure 18:
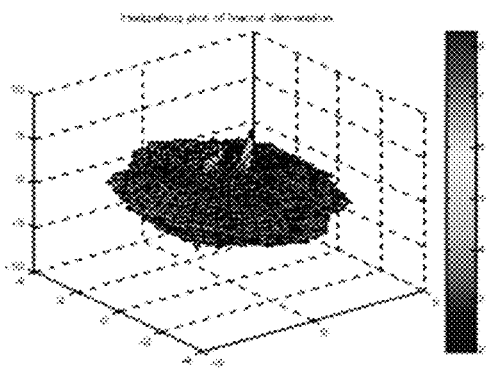
Figure 18:
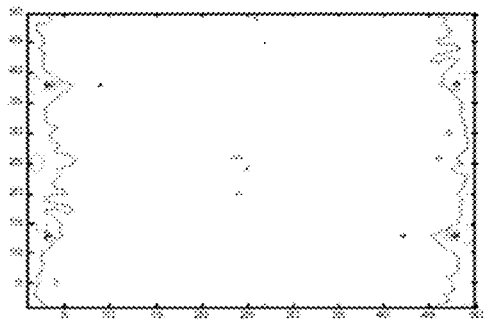
Figure 19:
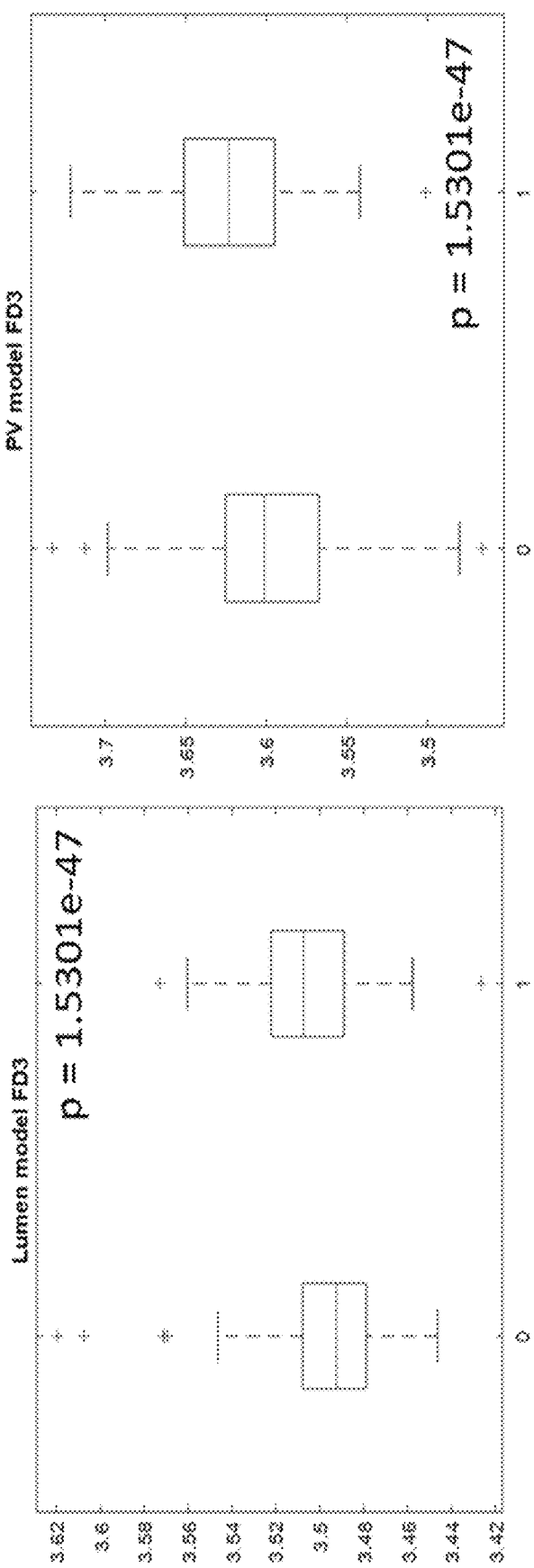
FIG. 19 illustrates boxplots of 3D fractal feature for the lumen model (left) and the PV model (right), in connection with various aspects discussed herein.

FIGS. 16-19 illustrate example images, charts, and plots in connection with the framework of the third example use case. Referring to FIG. 16, illustrated are example CT scans of an AF+ patient (top) and an AF− patient (bottom), in connection with various aspects discussed herein. Referring to FIG. 17, illustrated are example binary images of the CT scans of FIG. 9 based (AF+ in the left column and AF− in the right column) on two segmentation masks, the left atrial lumen model (top row) and PV model (bottom row), in connection with various aspects discussed herein. The lumen model consisted of the left atrium body and the ostia of the PVs. The PV model consisted of the left atrium body and the full structure of PVs visible on CT. Referring to FIG. 18, illustrated are charts showing 3D fractal analysis of lumen models for AF+ (top) and AF− (bottom), in connection with various aspects discussed herein. Fractal analysis was used to quantify morphological variations within each lumen and PV model. 3D fractal features were extracted from 3D binary images using a spectral density function to characterize self-similarity and heterogeneity of the models. Referring to FIG. 19, illustrated are boxplots of 3D fractal feature for the lumen model (left) and the PV model (right), in connection with various aspects discussed herein. Fractal features were compared between the AF+ and AF− groups.

Results: Statistically significant differences were observed for 3D fractal analysis of Lumen and PV models, distinguishing between AF+ and AF− (p<1.0e-25 in both cases, as seen in FIG. 19). Greater values of fractal features are reflective of greater levels of anatomic complexity and surface variation.

Conclusion: 3D fractal analysis can represent morphological characteristics of the left atrium and pulmonary veins on CT scans, which may be useful in predicting recurrence of AF post-ablation.

Clinical Relevance: Fractal analysis of left atrium and pulmonary vein morphology on CT scans can predict AF recurrence following catheter ablation. In various embodiments, these techniques can be employed to impact patient selection and ablation strategies.

Example Use Case 4: Machine Learning Derived Features of Left Atrium, Pulmonary Veins, and Myocardium on CT Scans is Associated with Risk of Recurrence of Atrial Fibrillation Post-Ablation The following discussion provides example embodiments in connection with a fourth example use case involving training, validation, and testing of machine learning models to predict recurrence of atrial fibrillation based at least in part on machine learning derived fractal features.

Figure 20:
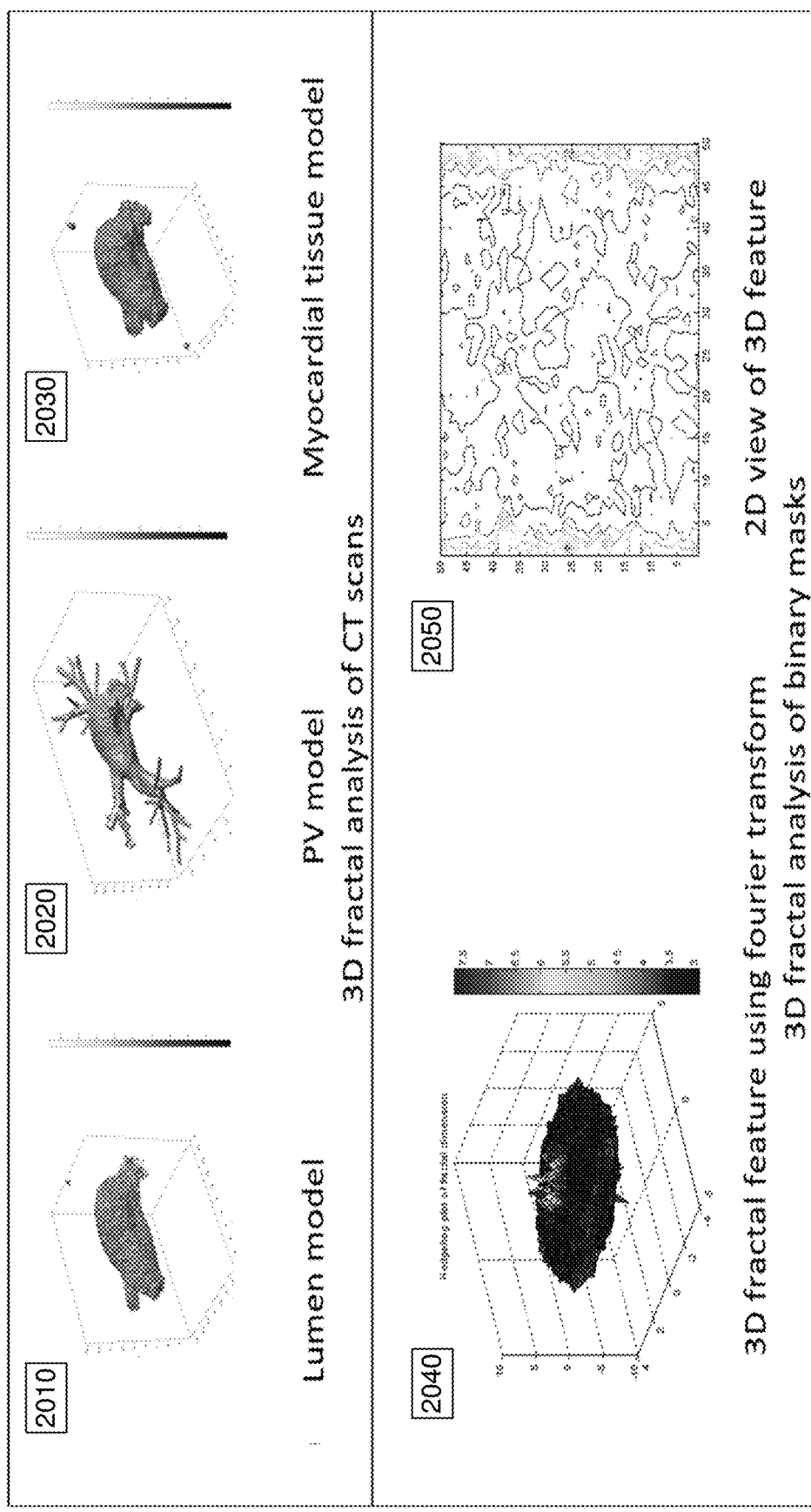
FIG. 20 illustrates example images and charts showing the lumen model, PV model, myocardial tissue model, a hedgehog chart of 3D fractal feature using Fourier transform, and a 2D view of the 3D fractal feature, in connection with various aspects discussed herein.

Referring to FIG. 20, illustrated are example images and charts showing the lumen model (2010), PV model (2020), myocardial tissue model (2030), a hedgehog chart of 3D fractal feature using Fourier transform (2040), and a 2D view of the 3D fractal feature (2050), in connection with various aspects discussed herein.

Overview: Pre-ablation contrast CT scans were obtained from patients undergoing AF ablation. AF recurrence was defined at 3 months to 1 year. Three segmentation models were created from each CT scan. The LA lumen model consisted of the volume defined by the LA lumen extending to the PV ostia. The PV model consisted of the LA lumen and the full structure of PVs visible on CT. The LA myocardial tissue model consisted of the LA wall. 3D fractal analysis was applied to these models to quantify morphological variation. 7 features for each model were extracted using power low and spectral density function to characterize self-similarity and heterogeneity of the models. 119 patients (67 with and 52 without AF recurrence) were used to train random forest classifiers that were tested on a separate dataset of 66 patients (20 with and 46 without AF recurrence). Prediction performance was quantified by Area Under the Receiver Operating Characteristic Curve (AUC).

Results: 3D fractal features characterizing LA and PV morphology predicted AF recurrence after ablation. On the test set, The PV model had best prediction (AUC 0.80), followed by the LA volume model (AUC 0.75), the myocardial tissue model (AUC 0.71).

Conclusions: Fractal analysis of morphological variations in LA and PV anatomy can be used to predict AF recurrence following ablation.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing models or classifiers to determine a risk of recurrence of atrial fibrillation (AF) post ablation, based at least in part on fractal features of CT scans or associated binary masks that are not perceivable by the human eye, and involve computation that cannot be practically performed in the human mind. As one example, machine learning classifiers as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 21:
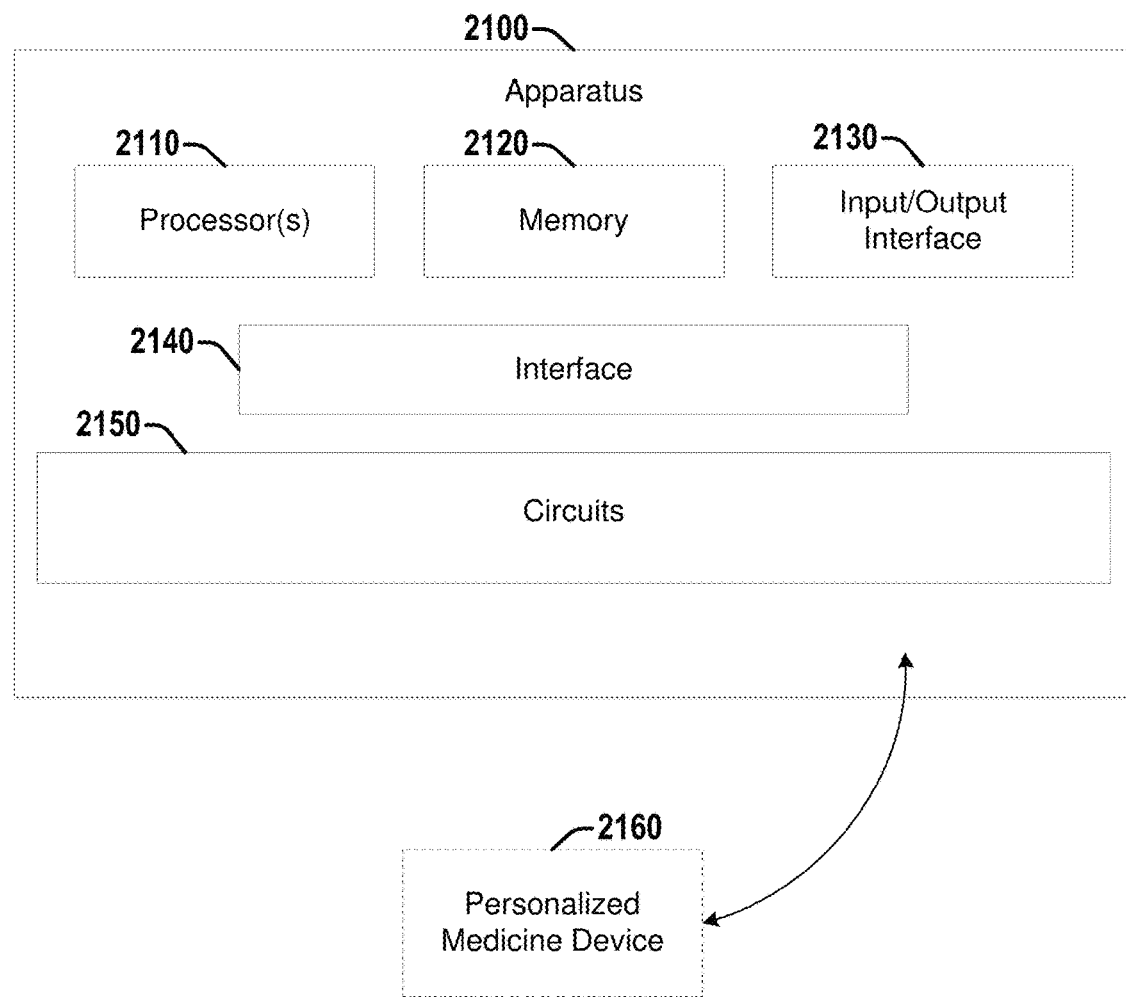
FIG. 21 illustrates a diagram of an example apparatus that can facilitate training and/or employing machine learning classifier(s) to determine a risk of recurrence of atrial fibrillation (AF) post-ablation based at least in part on fractal features, according to various embodiments discussed herein.

Referring to FIG. 21, illustrated is a diagram of an example apparatus 2100 that can facilitate training and/or employing machine learning classifier(s) to determine a risk of recurrence of atrial fibrillation (AF) post-ablation based at least in part on fractal features, according to various embodiments discussed herein. Apparatus 2100 can be configured to perform various techniques discussed herein, for example, various operations discussed in connection with sets of operations 100, 200, and/or 300. Apparatus 2100 can comprise one or more processors 2110 and memory 2120. Processor(s) 2110 can, in various embodiments, comprise circuitry such as, but not limited to, one or more single-core or multi-core processors. Processor(s) 2110 can include any combination of general-purpose processors and dedicated processors (e.g., graphics processors, application processors, etc.). The processor(s) can be coupled with and/or can comprise memory (e.g., of memory 2120) or storage and can be configured to execute instructions stored in the memory 2120 or storage to enable various apparatus, applications, or operating systems to perform operations and/or methods discussed herein. Memory 2120 can be configured to store one or more cardiac CT scans. Each of the CT scan(s) can comprise a plurality of pixels or voxels, each pixel or voxel having an associated intensity. Memory 2120 can be further configured to store additional data involved in performing operations discussed herein, such as information employed in various methods (e.g., 100, 200, 300, etc.) discussed in greater detail herein.

Apparatus 2100 can also comprise an input/output (I/O) interface 2130 (e.g., associated with one or more I/O devices), a set of circuits 2150, and an interface 2140 that connects the processor(s) 2110, the memory 2120, the I/O interface 2130, and the set of circuits 2150. I/O interface 2130 can be configured to transfer data between memory 2120, processor 2110, circuits 2150, and external devices, for example, a medical imaging device (e.g., CT system, etc.), and/or one or more remote devices for receiving inputs and/or providing outputs to a clinician, patient, etc., such as optional personalized medicine device 2160.

The processor(s) 2110 and/or one or more circuits of the set of circuits 2150 can perform one or more acts associated with a method or set of operations discussed herein, such as set of operations 100, 200, and/or 300. In various embodiments, different acts (e.g., different operations of a set of operations) can be performed by the same or different processor(s) 2110 and/or one or more circuits of the set of circuits 2150.

Apparatus 2100 can optionally further comprise personalized medicine device 2160. Apparatus 2100 can be configured to provide a prognosis (e.g., predicted outcome post-ablation) for a patient determined based at least in part on fractal features as discussed herein, and/or other data to personalized medicine device 2160. Personalized medicine device 2160 may be, for example, a computer assisted diagnosis (CADx) system or other type of personalized medicine device that can be used to facilitate monitoring and/or treatment of an associated medical condition. In some embodiments, processor(s) 2110 and/or one or more circuits of the set of circuits 2150 can be further configured to control personalized medicine device 2160 to display the prognosis for a clinician or the patient or other data on a computer monitor, a smartphone display, a tablet display, or other displays.

Examples herein can include subject matter such as an apparatus, a CT system/apparatus, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: accessing a Computerized Tomography (CT) scan of a heart of a patient with Atrial Fibrillation (AF); generating a binary mask of at least a portion of the CT scan; computing one or more radiomic fractal-based features from at least one of the binary mask or the portion of the CT scan; providing the one or more radiomic fractal-based features to a trained machine learning (ML) classifier; and receiving a prediction from the trained ML classifier of whether or not the AF will recur after AF ablation, wherein the prediction is based at least in part on the one or more radiomic fractal-based features.

Example 2 comprises the subject matter of any variation of any of example(s) 1, wherein the operations further comprise providing one or more clinical features associated with the patient to the trained ML classifier, wherein the prediction is based at least in part on the one or more clinical features.

Example 3 comprises the subject matter of any variation of any of example(s) 2, wherein the one or more clinical features comprise one or more of: an AF type of the AF, an age of the patient, a catheter technique of the AF ablation, or a hypertension status of the patient.

Example 4 comprises the subject matter of any variation of any of example(s) 1-3, wherein the trained ML classifier is one of a Support Vector Machine ML classifier or a random forest ML classifier.

Example 5 comprises the subject matter of any variation of any of example(s) 1-4, wherein the portion of the CT scan comprises a left atrium (LA) body of the heart and ostia of pulmonary veins (PVs) of the heart.

Example 6 comprises the subject matter of any variation of any of example(s) 1-5, wherein the portion of the CT scan comprises a left atrium (LA) body of the heart and all pulmonary veins (PV) structures of the heart on the CT scan.

Example 7 comprises the subject matter of any variation of any of example(s) 1-6, wherein the portion of the CT scan comprises a wall of a left atrium (LA) body of the heart.

Example 8 comprises the subject matter of any variation of any of example(s) 1-7, wherein the one or more radiomic fractal-based features comprise at least one of: a median of a three-dimensional (3D) fractal dimension (FD), a mean of a two-dimensional (2D) FD, a skewness of a 3D FD, or an entropy.

Example 9 is an apparatus, comprising: a memory configured to store a Computerized Tomography (CT) scan of a heart of a patient with Atrial Fibrillation (AF); and one or more processors configured to: generate a binary mask of at least a portion of the CT scan; compute one or more radiomic fractal-based features from at least one of the binary mask or the portion of the CT scan; provide the one or more radiomic fractal-based features to a trained machine learning (ML) classifier; and receive a prediction from the trained ML classifier of whether or not the AF will recur after AF ablation, wherein the prediction is based at least in part on the one or more radiomic fractal-based features.

Example 10 comprises the subject matter of any variation of any of example(s) 9, wherein the one or more processors are further configured to provide one or more clinical features associated with the patient to the trained ML classifier, wherein the prediction is based at least in part on the one or more clinical features.

Example 11 comprises the subject matter of any variation of any of example(s) 10, wherein the one or more clinical features comprise one or more of: an AF type of the AF, an age of the patient, a catheter technique of the AF ablation, or a hypertension status of the patient.

Example 12 comprises the subject matter of any variation of any of example(s) 9-11, wherein the trained ML classifier is one of a Support Vector Machine ML classifier or a random forest ML classifier.

Example 13 comprises the subject matter of any variation of any of example(s) 9-12, wherein the portion of the CT scan comprises a left atrium (LA) body of the heart and ostia of pulmonary veins (PVs) of the heart.

Example 14 comprises the subject matter of any variation of any of example(s) 9-13, wherein the portion of the CT scan comprises a left atrium (LA) body of the heart and all pulmonary veins (PV) structures of the heart on the CT scan.

Example 15 comprises the subject matter of any variation of any of example(s) 9-14, wherein the portion of the CT scan comprises a wall of a left atrium (LA) body of the heart.

Example 16 comprises the subject matter of any variation of any of example(s) 9-15, wherein the one or more radiomic fractal-based features comprise at least one of: a median of a three-dimensional (3D) fractal dimension (FD), a mean of a two-dimensional (2D) FD, a skewness of a 3D FD, or an entropy.

Example 17 is a non-transitory computer-readable medium storing computer-executable instructions that, when executed, cause a processor to perform operations, comprising: accessing a training set comprising a plurality of Computerized Tomography (CT) scans, wherein each CT scan of the training set is a CT scan of a heart of an associated patient with Atrial Fibrillation (AF), wherein each CT scan of the training set is associated with an associated known outcome after AF ablation, wherein the associated outcome is one of recurrence or non-recurrence; for each CT scan of the training set: generating an associated binary mask of at least a portion of that CT scan; and computing an associated value for each of a plurality of radiomic fractal-based features from at least one of the associated binary mask or the portion of that CT scan; determining one or more best features for determining recurrence or non-recurrence of AF after AF ablation from among a set of features comprising the plurality of radiomic fractal-based features, wherein the one or more best features are determined based at least on: the associated known outcome after AF ablation for each CT scan of the training set and the associated value for each of the plurality of radiomic fractal-based features for each CT scan of the training set; and constructing a machine learning (ML) classifier configured to determine a likely outcome after AF ablation for an additional CT scan based at least on the one or more best features.

Example 18 comprises the subject matter of any variation of any of example(s) 17, wherein the one or more best features are determined based at least in part on one or more of a Wilcoxon rank-sum test or a minimum redundancy maximum relevance algorithm.

Example 19 comprises the subject matter of any variation of any of example(s) 17-18, wherein the set of features comprises a plurality of clinical features, and wherein the one or more best features are determined based at least on an associated value for each of the plurality of clinical features for each CT scan of the training set.

Example 20 comprises the subject matter of any variation of any of example(s) 17-19, wherein the one or more radiomic fractal-based features comprise at least one of: a median of a three-dimensional (3D) fractal dimension (FD), a mean of a two-dimensional (2D) FD, a skewness of a 3D FD, or an entropy.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
   accessing a Computerized Tomography (CT) scan of a heart of a patient with Atrial Fibrillation (AF);
   generating a binary mask of at least a portion of the CT scan;
   computing one or more radiomic fractal-based features from at least one of the binary mask or the portion of the CT scan;
   providing the one or more radiomic fractal-based features to a trained machine learning (ML) classifier;
   providing one or more clinical features associated with the patient to the trained ML classifier; and
   receiving a prediction from the trained ML classifier of whether or not the AF will recur after AF ablation, wherein the prediction is based at least in part on the one or more radiomic fractal-based features and at least in part on the one or more clinical features, and wherein the one or more clinical features comprise one or more of: an AF type of the AF, an age of the patient, a catheter technique of the AF ablation, or a hypertension status of the patient.

2. The non-transitory computer-readable medium of claim 1, wherein the trained ML classifier is one of a Support Vector Machine ML classifier or a random forest ML classifier.

3. The non-transitory computer-readable medium of claim 1, wherein the portion of the CT scan comprises a left atrium (LA) body of the heart and ostia of pulmonary veins (PVs) of the heart.

4. The non-transitory computer-readable medium of claim 1, wherein the portion of the CT scan comprises a left atrium (LA) body of the heart and all pulmonary veins (PV) structures of the heart on the CT scan.

5. The non-transitory computer-readable medium of claim 1, wherein the portion of the CT scan comprises a wall of a left atrium (LA) body of the heart.

6. The non-transitory computer-readable medium of claim 1, wherein the one or more radiomic fractal-based features comprise at least one of: a median of a three-dimensional (3D) fractal dimension (FD), a mean of a two-dimensional (2D) FD, a skewness of a 3D FD, or an entropy.

7. An apparatus, comprising:
   a memory configured to store a Computerized Tomography (CT) scan of a heart of a patient with Atrial Fibrillation (AF); and
   one or more processors configured to:
   generate a binary mask of at least a portion of the CT scan;
   compute one or more radiomic fractal-based features from at least one of the binary mask or the portion of the CT scan;
   provide the one or more radiomic fractal-based features to a trained machine learning (ML) classifier;
   provide one or more clinical features associated with the patient to the trained ML classifier; and
   receive a prediction from the trained ML classifier of whether or not the AF will recur after AF ablation, wherein the prediction is based at least in part on the one or more radiomic fractal-based features and at least in part on the one or more clinical features, and wherein the one or more clinical features comprise one or more of: an AF type of the AF, an age of the patient, a catheter technique of AF ablation, or a hypertension status of the patient.

8. The apparatus of claim 7, wherein the trained ML classifier is one of a Support Vector Machine ML classifier or a random forest ML classifier.

9. The apparatus of claim 7, wherein the portion of the CT scan comprises a left atrium (LA) body of the heart and ostia of pulmonary veins (PVs) of the heart.

10. The apparatus of claim 7, wherein the portion of the CT scan comprises a left atrium (LA) body of the heart and all pulmonary veins (PV) structures of the heart on the CT scan.

11. The apparatus of claim 7, wherein the portion of the CT scan comprises a wall of a left atrium (LA) body of the heart.

12. The apparatus of claim 7, wherein the one or more radiomic fractal-based features comprise at least one of: a median of a three-dimensional (3D) fractal dimension (FD), a mean of a two-dimensional (2D) FD, a skewness of a 3D FD, or an entropy.

13. A non-transitory computer-readable medium storing computer-executable instructions that, when executed, cause a processor to perform operations, comprising:
   accessing a training set comprising a plurality of Computerized Tomography (CT) scans, wherein each CT scan of the training set is a CT scan of a heart of an associated patient with Atrial Fibrillation (AF), wherein each CT scan of the training set is associated with an associated known outcome after AF ablation, wherein the associated outcome is one of recurrence or non-recurrence;
   for each CT scan of the training set:
   generating an associated binary mask of at least a portion of that CT scan; and
   computing an associated value for each of a plurality of radiomic fractal-based features from at least one of the associated binary mask or the portion of that CT scan;
   determining one or more best features for determining recurrence or non-recurrence of AF after AF ablation from among a set of features comprising the plurality of radiomic fractal-based features, wherein the one or more best features are determined based at least on: the associated known outcome after the AF ablation for each CT scan of the training set and the associated value for each of the plurality of radiomic fractal-based features for each CT scan of the training set; and constructing a machine learning (ML) classifier configured to determine a likely outcome after the AF ablation for an additional CT scan based at least on the one or more best features and based on one or more clinical features associated with the associated patient, wherein the one or more clinical features comprise one or more of: an AF type of the AF. an age of the associated patient, a catheter technique of the AF ablation, or a hypertension status of the associated patient.

14. The non-transitory computer-readable medium of claim 13, wherein the one or more best features are determined based at least in part on one or more of a Wilcoxon rank-sum test or a minimum redundancy maximum relevance algorithm.

15. The non-transitory computer-readable medium of claim 13, wherein the set of features comprises a plurality of clinical features, and wherein the one or more best features are determined based at least on an associated value for each of the plurality of clinical features for each CT scan of the training set.

16. The non-transitory computer-readable medium of claim 13, wherein the plurality of radiomic fractal-based features comprise at least one of: a median of a three-dimensional (3D) fractal dimension (FD), a mean of a two-dimensional (2D) FD, a skewness of a 3D FD, or an entropy.

17. The non-transitory computer-readable medium of claim 13, wherein the portion of the CT scan comprises a left atrium (LA) body of the heart and ostia of pulmonary veins (PVs) of the heart.

18. The non-transitory computer-readable medium of claim 13, wherein the portion of the CT scan comprises a left atrium (LA) body of the heart and all pulmonary veins (PV) structures of the heart on the CT scan.

19. The non-transitory computer-readable medium of claim 13, wherein the portion of the CT scan comprises a wall of a left atrium (LA) body of the heart.

20. The non-transitory computer-readable medium of claim 13, wherein the one or more best features are determined with a Random Forest classifier.

* * * * *